US012573498B2

(12) United States Patent
Jodoin et al.

(10) Patent No.: US 12,573,498 B2
(45) Date of Patent: Mar. 10, 2026

(54) DETERMINATION OF WHITE-MATTER NEURODEGENERATIVE DISEASE BIOMARKERS

(71) Applicant: Imeka Solutions Inc., Sherbrooke (CA)

(72) Inventors: Pierre-Marc Jodoin, Eastman (CA); Maxime Descoteaux, Magog (CA)

(73) Assignee: Imeka Solutions Inc., Sherbrooke (CA)

( * ) Notice: Subject to any disclaimer, the term of this patent is extended or adjusted under 35 U.S.C. 154(b) by 1155 days.

(21) Appl. No.: 17/503,253

(22) Filed: Oct. 15, 2021

(65) Prior Publication Data

US 2023/0022257 A1     Jan. 26, 2023

Related U.S. Application Data

(60) Provisional application No. 63/222,914, filed on Jul. 16, 2021.

(51) Int. Cl.
*A61B 5/00*          (2006.01)
*G06N 3/08*          (2023.01)
              (Continued)

(52) U.S. Cl.
CPC .............. *G16H 30/40* (2018.01); *G06N 3/08* (2013.01); *G16H 70/60* (2018.01)

(58) Field of Classification Search
CPC ...................................................... G06N 3/08
See application file for complete search history.

(56) References Cited

U.S. PATENT DOCUMENTS 6,463,315 B1     10/2002   Klingberg et al.
2012/0280686 A1  11/2012   White et al.
              (Continued)

OTHER PUBLICATIONS

A. A. Vijayakumari, D. Parker, Y. Osmanlioglu, J. A. Alappatt, J. Whyte, R. Diaz-Arrastia, J. J. Kim, and R. Verma, "Free water volume fraction: An imaging biomarker to characterizemoderate-to-severe traumatic brain injury," J. Neurotrauma, vol. 38, No. 19, pp. 2698-2705, Sep. 2021.
              (Continued)

*Primary Examiner* — Joel F Brutus
(74) *Attorney, Agent, or Firm* — Torrey Pines Law Group PC

(57) ABSTRACT

A computer system may receive medical-imaging data associated with at least an individual. Then, the computer system may compute, based at least in part on the medical-imaging data, a set of white-matter disease biomarkers for different neurological anatomical regions, where, for a given neurological anatomical region, the set of white-matter disease biomarkers includes: an apparent fiber density that corresponds to a total intra-axonal volume, an amount of free water, and a demyelination metric. Next, the computer system may provide feedback information associated with at least the individual based at least in part on interrelationships among the computed set of white-matter disease biomarkers in different neurological anatomical regions. For example, the feedback information may include: diagnostic information, information associated with disease progression (such as a disease stage), information regarding efficacy of a treatment, or a treatment recommendation (e.g., based at least in part on the disease stage).

20 Claims, 40 Drawing Sheets

(51) Int. Cl.
    *G16H 30/40*        (2018.01)
    *G16H 70/60*        (2018.01)

(56) References Cited

U.S. PATENT DOCUMENTS

| | | | |
|---|---|---|---|
| 2013/0004049 | A1 | 1/2013 | Weeden |
| 2014/0294270 | A1 | 10/2014 | Schneider et al. |
| 2015/0073258 | A1* | 3/2015 | Mazer ................ G01R 33/4828 |
| | | | 600/410 |
| 2019/0150822 | A1 | 5/2019 | Wang et al. |
| 2021/0186409 | A1* | 6/2021 | Lee ........................ A61B 5/055 |

OTHER PUBLICATIONS

A. Zarkali, P. McColgan, L.-A. Leyland, A. J. Lees, G. Rees, and R. S. Weil, "Fiber-specific white matter reductions in Parkinson hallucinations and visual dysfunction," Neurology, vol. 94, No. 14, pp. e1525-e1538, Apr. 2020.

A.-M. Beaudoin, F. Rheault, G. Theaud, F. Laberge, K. Whittingstall, A. Lamontagne, and M. Descoteaux, "Modern technology in multi-shell diffusion MRI reveals diffuse white matter changes in young adults with relapsing-remitting multiple sclerosis," Frontiers in Neuroscience, vol. 15, Aug. 2021.

Aung WY, Mar S, Benzinger TL. Diffusion tensor MRI as a biomarker in axonal and myelin damage. Imaging Med. 2013;5(5):427-440. doi: 10.2217/iim.13.49.

C. Andica, K. Kamagata, Y. Saito, W. Uchida, S. Fujita, A. Hagiwara, T. Akashi, A. Wada, T. Ogawa, T. Hatano, N. Hattori, and S. Aoki, "Fiber-specific white matter alterations in early-stage tremor-dominant Parkinson's disease," NPJ Parkinson's Disease, vol. 7, p. 51, Jun. 2021.

C. Laule, I. M. Vavasour, S. H. Kolind, D. K. B. Li, T. L. Traboulsee, G. R. W. Moore, and A. L. MacKay, "Magnetic resonance imaging of myelin," Neurotherapeutics, vol. 4, No. 3, pp. 460-484, Jul. 2007.

Charlton RA, Barrick TR, McIntyre DJ, Shen Y, O'Sullivan M, Howe FA, Clark CA, Morris RG, Markus HS. White matter damage on diffusion tensor imaging correlates with age-related cognitive decline. Neurology. Jan. 24, 2006;66(2):217-22. doi: 10.1212/01.wnl.0000194256.15247.83. PMID: 16434657.

D. C. Dean III, J. Sojkova, S. Hurley, S. Kecskemeti, O. Okonkwo, B. B. Bendlin, F. Theisen, S. C. Johnson, A. L. Alexander, and C. L. Gallagher, "Alterations of myelin content in Parkinson's disease: A cross-sectional neuroimaging study," PLOS One, vol. 11, No. 10, p. e0163774, Oct. 2016.

Wright DK, Johnston LA, Kershaw J, Ordidge R, O'Brien TJ, Shultz SR. Changes in Apparent Fiber Density and Track-Weighted Imaging Metrics in White Matter following Experimental Traumatic Brain Injury. J Neurotrauma. Jul. 1, 2017;34(13):2109-2118. doi: 10.1089/neu.2016.4730. Epub Apr. 13, 2017. PMID: 28152648.

D. Raffelt, J. D. Tournier, S. Crozier, K. Ellis, R. Martins, V. Villemagne, C. Masters, D. Ames, C. Rowe, O. Salvado, and A. Connelly, "Apparent fibre density: A novel MRI approach that identifies specific white matter tracts affected in Alzheimer's disease and MCI," Alzheimer's & Dementia, vol. 8, No. 4S_Part_19, 2012.

E. Ofori, O. Pasternak, P. J. Planetta, R. Burciu, A. Snyder, M. Febo, T. E. Golde, M. S. Okun, and D. E. Vaillancourt, "Increased free-water in the substantia nigra of Parkinson's disease: a single-site and multi-site study," Neurobiology of Aging, vol. 36, No. 2, pp. 1097-1104, Feb. 2016.

F. Ji, O. Pasternak, S. Liu, Y. Miin Loke, B. Linn Choo, S. Hilal, X. Xu, M. Kamran Ikram, N. Venketasubramanian, C. Li-Hsian Chen, J. Zhou "Distinct white matter microstructural abnormalities and extracellular water increases relate to cognitive impairment in Alzheimer's disease with and without cerebrovascular disease", Alzheimers Res Ther. Aug. 17, 2017;9(1):63.

G. Arribarat, O Pasternak, A De Barros, M Galitzky, O Rascol, P Péran. "Substantia nigra locations of iron-content, free-water and mean diffusivity abnormalities in moderate stage Parkinson's disease". Parkinsonism Relat Disord. 2019; 65:146-152.

Hagiwara, A. et al. Analysis of White Matter Damage in Patients with Multiple Sclerosis via a Novel In Vivo Magnetic Resonance Method for Measuring Myelin, Axons, and G-ratio. AJNR Am J Neuroradiol 38, 1934-1940.

Hoy, A. R., Ly, M., Carlsson, C. M., Okonkwo, O. C., Zetterberg, H., Blennow, K., Sager, M. A., Asthana, S., Johnson, S. C., Alexander, A. L., & Bendlin, B. B. (2017). "Microstructural white matter alterations in preclinical Alzheimer's disease detected using free water elimination diffusion tensor imaging". PLoS One, 12(3).

K. Chary, O. Narvaez, R. A. Salo, I. San Martin Molina, J. Tohka, M. Aggarwal, O. Gröhn, and A. Sierra, "Microstructural tissue changes in a rat model of mild traumatic brain injury," Frontiers in Neuroscience, vol. 15, Nov. 2021.

M. Bergamino, R. R. Walsh & A. M. Stokes "Free-water diffusion tensor imaging improves the accuracy and sensitivity of white matter analysis in Alzheimer's disease", Scientific Reports vol. 11, Article No. 6990 (2021).

M. Dumont 1, M. Roy, P-M Jodoin, F. C Morency, J-C Houde, Z. Xie, C. Bauer, T. A Samad, K. R A Van Dijk, J. A Goodman, M. Descoteaux "Free Water in White Matter Differentiates MCI and AD From Control Subjects Front Aging" Neurosci. Oct. 2, 2019;11:270.

Margoni M, Petracca M, Schiavi S, Fabian M, Miller A, Lublin FD, Inglese M. Axonal water fraction as marker of white matter injury in primary-progressive multiple sclerosis: a longitudinal study. Eur J Neurol. Aug. 2019;26(8):1068-1074. doi: 10.1111/ene.13937. Epub Mar. 25, 2019. PMID: 30761708.

P. Maillard, E. Fletcher, B. Singh, O. Martinez, D. K. Johnson, J. M. Olichney, S. T. Farias, C. DeCarli "Cerebral white matter free water: A sensitive biomarker of cognition and function", Neurology. May 7, 2019;92(19).

Planetta, P. J., Ofori, E., Pasternak, O., Burciu, R. G., Shukla, P., DeSimone, J. C., Okun, M. S., McFarland, N. R., & Vaillancourt, D. E. (2016). "Free-water imaging in Parkinson's disease and atypical parkinsonism". Brain, 139(2), 495-508.

R. Mito, D. Raffelt, T. Dhollander, D. N. Vaughan, J.-D. Tournier, O. Salvado, A. Brodtmann, C. C. Rowe, V. L. Villemagne, and A. Connelly, "Fibre-specific white matter reductions in Alzheimer's disease and mild cognitive impairment," Brain, vol. 141, No. 3, pp. 888-902, Mar. 2018.

R. Rahmanzadeh, P.-J. Lu, M. Barakovic, M. Weigel, P. Maggi, T. D. Nguyen, S. Schiavi, A. Daducci, F. La Rosa, S. Schaedelin, M. Absinta, D. S. Reich, P. Sati, Y. Wang, M. B. Cuadra, E.-W. Radue, J. Kuhle, L. Kappos, and C. Granziera, "Myelin and axon pathology in multiple sclerosis assessed by myelin water and multi-shell diffusion imaging," Brain, vol. 144, No. 6, pp. 1684-1696, Mar. 2021.

S. Abel, I. Vavasour, L. E. Lee, P. Johnson, S. Ristow, N. Ackermans, J. Chan, H. Cross, C. Laule, A. Dvorak, A. Schabas, E. Hernández-Torres, R. Tam, A. J. Kuan, S. A. Morrow, J. Wilken, A. Rauscher, V. Bhan, A.-L. Sayao, V. Devonshire, D. K. B. Li, R. Carruthers, A. Traboulsee, and S. H. Kolind, "Associations between findings from myelin water imaging and cognitive performance among individuals with multiple sclerosis," JAMA Network Open, vol. 3, No. 9, p. e2014220, Sep. 2020.

S. E. Nasrabady, B. Rizvi, J. E. Goldman, and A. M. Brickman, "White matter changes in Alzheimer's disease: a focus on myelin and oligodendrocytes," Acta Neuropathologica Communications, vol. 6, No. 22, 2018.

S. Gajamange, D. Raffelt, T. Dhollander, E. Lui, A. van der Walt, T. Kilpatrick, J. Fielding, A. Connelly, and S. Kolbe, "Fibre-specific white matter changes in multiple sclerosis patients with optic neuritis," NeuroImage: Clinical, vol. 17, pp. 60-68, Sep. 2017.

T. Veale, I. B. Malone, T. Poole, T. D. Parker, C. F. Slattery, R. W. Paterson, A. J. M. Foulkes, D. L. Thomas, J. M. Schott, H. Zhang, and others, "Loss and dispersion of superficial white matter in Alzheimer's disease: a diffusion MRI study," Brain Communications, vol. 3, No. 4, 2021.

X. Luo, S. Wang, Y. Jiaerken, K. Li, Q. Zeng, R. Zhang, C. Wang, X. Xu, D. Wu, P. Huang, M. Zhang, and the Alzheimer's Disease Neuroimaging Initiative (ADNI), "Distinct fiber-specific white mat-

(56)                   References Cited

OTHER PUBLICATIONS ter reductions pattern in early- and late-onset Alzheimer's disease,"
Aging (Albany NY), vol. 13, No. 9, pp. 12410-12430, Apr. 2021.

* cited by examiner

TRAINING (PHASE 1): ENCODE A REFERENCE TRACTOGRAM

AUTOENCODER

LATENT SPACE

TRAINING (PHASE 2): ENCODE A NOISY TRACTOGRAM

TRAINING (PHASE 3): DETERMINE WHICH LATENT VECTOR IS CLOSE TO A REFERENCE TRACTOGRAM

AUTOENCODER

LATENT SPACE

TESTING (PHASE 1): ENCODE FIBERS FROM ONE OR MORE BUNDLES

AUTOENCODER

LATENT SPACE

TESTING (PHASE 2): ENCODE A NOISY TRACTOGRAM

AUTOENCODER

LATENT SPACE

FIG. 20

TESTING (PHASE 3): DETERMINE WHICH LATENT VECTOR IS
CLOSE TO A REFERENCE TRACTOGRAM

AUTOENCODER

LATENT SPACE

* Loss of myelin
* Distorted myelin sheets
* Granulation of myelin

ALZHEIMER'S MOUSE MODEL 15 MONTHS MYELIN LOSS AND DESTRUCTION

HEALTHY CONTROL WHITE-MATTER TISSUE (FORNIX)

* Lower density of myelinated axons
* Dystrophic axons
* Increased variability in axonal size & shape

HEALTHY CONTROL
WHITE-MATTER TISSUE (FORNIX)

ALZHEIMER'S MOUSE MODEL 15
MONTHS AXON DISRUPTION AND LOSS

DETERMINATION OF WHITE-MATTER NEURODEGENERATIVE DISEASE BIOMARKERS

CROSS REFERENCE TO RELATED APPLICATIONS

This application claims priority under 35 U.S.C. 119(e) to: U.S. Provisional Application Ser. No. 63/222,914, "Determination of White-Matter Neurodegenerative Disease Biomarkers," filed on Jul. 16, 2021, by Pierre-Marc Jodoin, et al, the contents of which are herein incorporated by reference.

FIELD

The described embodiments relate to processing of medical images. Notably, the described embodiments relate to a processing of medical images to determine white-matter neurodegenerative-disease biomarkers using an analysis pipeline.

BACKGROUND

The central nervous system consists of the brain and the spinal cord, which each include grey matter and white matter. Grey matter consists primarily of neuronal cell bodies and controls muscular and sensory activity, attention, memory, thought, emotions and, more generally, the processing of information. White matter mainly consists of myelinated axons (which are sometimes referred to as 'tracts') that are arranged in bundles, which connect various grey matter areas (the locations of neuronal cell bodies) of the brain to each other, and carry nerve impulses between neurons. Myelin acts as an insulator, which allows electrical signals to jump, rather than course through an axon, thereby increasing the speed of transmission of nerve signals. While previously thought to be passive tissue, white matter affects learning and brain functions, modulates the distribution of action potentials, acts as a relay, and coordinates communication between different brain regions.

White matter is known or suspected to play a role in many neurodegenerative diseases, such as: multiple sclerosis, Alzheimer's disease, Parkinson's disease, amyotrophic lateral sclerosis, traumatic brain injury, alcohol-use disorders, etc. For example, multiple sclerosis is an inflammatory demyelinating disease of the central nervous system that affects white matter. In MS lesions, the myelin sheath around the white-matter axons is deteriorated by inflammation.

In principle, the study of white matter and, thus, understanding of neurodegenerative diseases have been advanced by improved imaging technology, such as diffusion magnetic resonance imaging (dMRI). However, in practice it remains difficult to analyze medical-imaging data to quantify white-matter microstructure and its deterioration because of neurodegenerative diseases.

SUMMARY

A computer system that computes a set of white-matter disease biomarkers is described. This computer may include: a computation device (such as a processor, a graphics processing unit or GPU, etc.) that executes program instructions; and memory that stores the program instructions. During operation, the computer system receives medical-imaging data associated with at least an individual. Then, the computer system computes, based at least in part on the medical-imaging data, the set of white-matter disease biomarkers for different neurological anatomical regions, where, for a given neurological anatomical region, the set of white-matter disease biomarkers includes: an apparent fiber density that corresponds to a total intra-axonal volume, an amount of free water, and a demyelination metric. Next, the computer system provides feedback information associated with at least the individual based at least in part on interrelationships among the computed set of white-matter disease biomarkers in different neurological anatomical regions.

In embodiments for Alzheimer's disease, Parkinson's disease, multiple sclerosis or traumatic brain injury, the interrelationships include: an increase in the amount of free water, a decrease in the apparent fiber density and an increase in the demyelination.

Moreover, for the given neurological anatomical region, the set of white-matter disease biomarkers may include: an amount of free water or a demyelination metric.

Note that the amount of free water may correspond to neuroinflammation, and/or the apparent fiber density may correspond to axonal disruption or axonal quality. Furthermore, the demyelination metric may include: an inverse free-water-corrected radial diffusivity, a ratio of spin-lattice relaxation time $(T_1)$ to spin-spin relaxation time $(T_2)$, a magnetization transfer ratio, or a myelin water fraction (MWF). The MWF may be the ratio of the signal amplitudes measured in or associated with two water compartments, a myelin water compartment and an extra-intra cellular water compartment.

Additionally, the set of white-matter disease biomarkers may be computed on a per-voxel basis and/or a per-neurological-fiber (or fixel) basis.

In some embodiments, the medical-imaging data includes diffusion magnetic resonance imaging (dMRI) data, magnetization transfer MRI, and/or quantitative MRI.

Moreover, the feedback information may include: diagnostic information, information associated with disease progression (such as a disease stage), information regarding efficacy of a treatment, or a treatment recommendation (e.g., based at least in part on the disease stage). For example, the diagnostic information may be associated with a neurological disease, including: multiple sclerosis, Alzheimer's disease, Parkinson's disease, amyotrophic lateral sclerosis, traumatic brain injury, an alcohol-use disorder, or another neurodegenerative disease.

Furthermore, the feedback information may be based at least in part on a volume of a neurological anatomical region in at least the individual, such as the hippocampus.

Additionally, the medical-imaging data may be associated with a population of cases and controls, which includes at least the individual, and the feedback information may be associated with the population.

In some embodiments, the feedback information is determined using a pretrained predictive model. For example, the pretrained predictive model may include: a machine-learning model or a neural network. Note that a given node in a given layer in the neural network may include an activation function, and the activation function may include: a rectified linear activation function (ReLU), a leaky ReLU, an exponential linear unit (ELU) activation function, a parametric ReLU, a tanh activation function, or a sigmoid activation function.

Moreover, the computer system may dynamically determine the neurological anatomical regions that are of interest based at least in part on changes (e.g., as a function of time relative to previously computed values for at least the individual) of the set of white-matter disease biomarkers and/or based at least in part on a type of disease (such as predetermined pathophysiology associated with a type of disease). Furthermore, the feedback information may be based at least in part on the dynamically determined neurological anatomical regions.

Another embodiment provides a computer for use, e.g., in the computer system.

Another embodiment provides a computer-readable storage medium for use with the computer or the computer system. When executed by the computer or the computer system, this computer-readable storage medium causes the computer or the computer system to perform at least some of the aforementioned operations.

Another embodiment provides a method, which may be performed by the computer or the computer system. This method includes at least some of the aforementioned operations.

This Summary is provided for purposes of illustrating some exemplary embodiments, so as to provide a basic understanding of some aspects of the subject matter described herein. Accordingly, it will be appreciated that the above-described features are examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

FIGS. 15-21 are drawings illustrating examples of a cleaning and bundling operation in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

Figure 1:
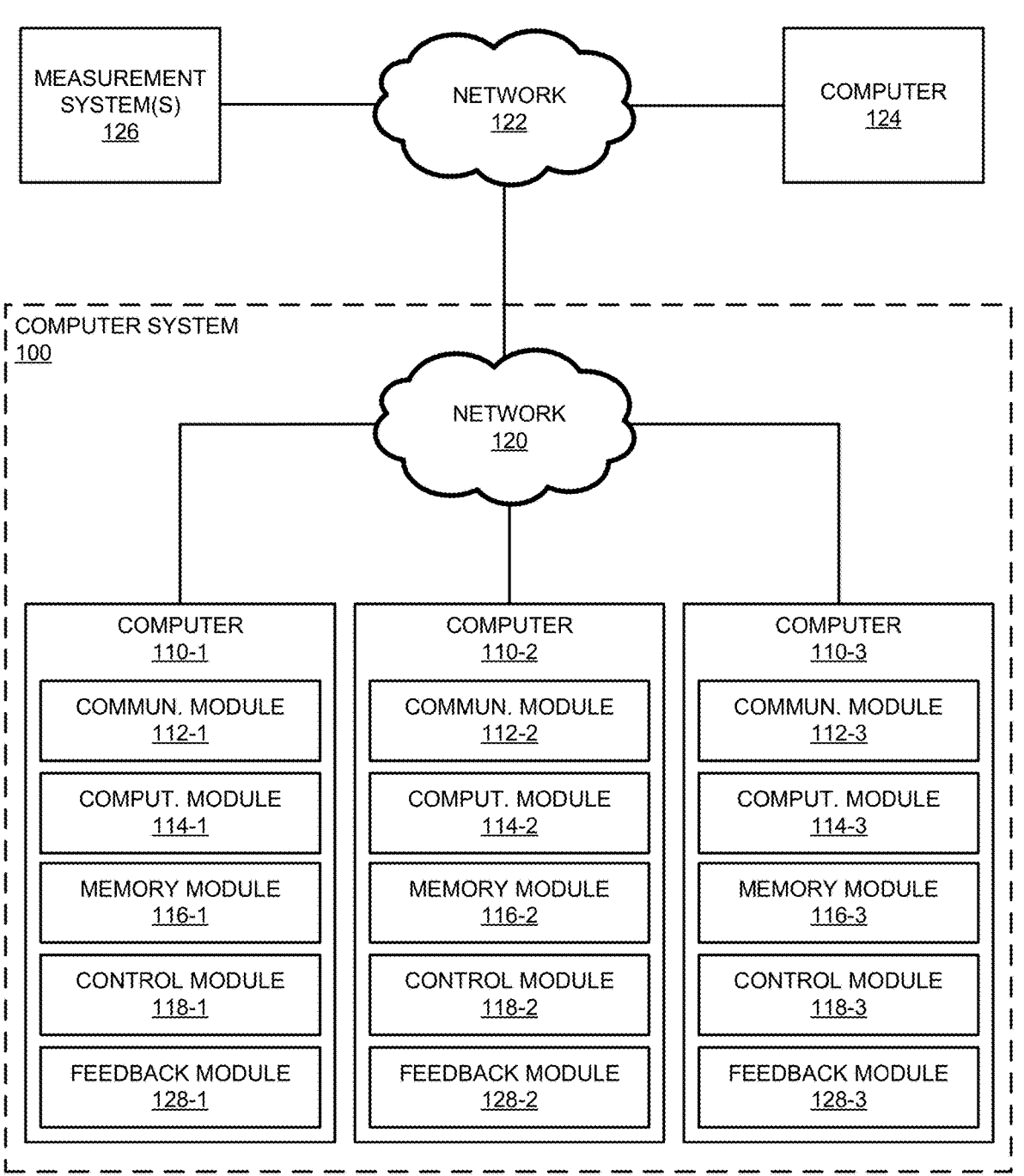
FIG. 1 is a block diagram illustrating an example of a computer system in accordance with an embodiment of the present disclosure.

A computer system that computes a set of white-matter disease biomarkers is described. This computer may include: a computation device (such as a processor, a graphics processing unit or GPU, etc.) that executes program instructions; and memory that stores the program instructions. During operation, the computer system may receive medical-imaging data (such as dMRI data) associated with at least an individual. Then, the computer system may compute, based at least in part on the medical-imaging data, the set of white-matter disease biomarkers for different neurological anatomical regions, where, for a given neurological anatomical region, the set of white-matter disease biomarkers includes: an apparent fiber density that corresponds to a total intra-axonal volume, an amount of free water, and a demyelination metric. Note that the set of white-matter disease biomarkers may be computed on a per-voxel basis and/or a per-neurological-fiber (or fixel) basis. Next, the computer may provide (e.g., using a pre-trained predictive model) feedback information associated with at least the individual based at least in part on interrelationships among the computed set of white-matter disease biomarkers in different neurological anatomical regions. For example, the feedback information may include: diagnostic information, information associated with disease progression (such as a disease stage), information regarding efficacy of a treatment, or a treatment recommendation (e.g., based at least in part on the disease stage).

By computing the set of white-matter disease biomarkers, these analysis techniques may address the problems associated with existing brain white-matter analysis techniques. Notably, the analysis techniques may provide quantitative insight into white-matter microstructure (corresponding to the local environment of each neurological fiber population) and its deterioration because of diseases, such as neurodegenerative diseases. Consequently, the analysis techniques may improve the accuracy and relevance of the feedback information, which may provide improved diagnosis, tracking of disease progression and treatment. Moreover, the computed set of white-matter disease biomarkers may enable further understanding of the diseases and their progression, and may facilitate the development of new treatments.

In the discussion that follows, the analysis techniques are used to analyze dMRI data. However, the analysis techniques may be used to analyze a wide variety of types of magnetic-resonance images (which may or may not involve MRI, e.g., free-induction-decay measurements), such as: magnetic resonance spectroscopy (MRS) with one or more types of nuclei, magnetic resonance spectral imaging (MRSI), magnetic resonance elastography (MRE), magnetic resonance thermometry (MRT), magnetic-field relaxometry and/or another magnetic resonance technique (e.g., functional MRI, metabolic imaging, molecular imaging, blood-flow imaging, diffusion-tensor imaging, etc.). More generally (and provided that the result neurological fibers are in the same reference as the analyzed images) the analysis techniques may be used to analyze measurement results from a wide variety of invasive and non-invasive imaging techniques, such as: X-ray measurements (such as X-ray imaging, X-ray diffraction or computed tomography at one or more wavelengths between 0.01 and 10 nm), neutron measurements (neutron diffraction), electron measurements (such as electron microscopy or electron spin resonance), optical measurements (such as optical imaging or optical spectroscopy that determines a complex index of refraction at one or more visible wavelengths between 300 and 800 nm or ultraviolet wavelengths between 10 and 400 nm), infrared measurements (such as infrared imaging or infrared spectroscopy that determines a complex index of refraction at one or more wavelengths between 700 nm and 1 mm), ultrasound measurements (such as ultrasound imaging in an ultrasound band of wavelengths between 0.2 and 1.9 mm), proton measurements (such as proton scattering), positron emission spectroscopy, positron emission tomography (PET), impedance measurements (such as electrical impedance at DC and/or an AC frequency) and/or susceptibility measurements (such as magnetic susceptibility at DC and/or an AC frequency).

We now describe embodiments of the analysis techniques. FIG. 1 presents a block diagram illustrating an example of a computer system 100. This computer system may include one or more computers 110. These computers may include: communication modules 112, computation modules 114, memory modules 116, and optional control modules 118. Note that a given module or engine may be implemented in hardware and/or in software.

Communication modules 112 may communicate frames or packets with data or information (such as measurement results or control instructions) between computers 110 via a network 120 (such as the Internet and/or an intranet). For example, this communication may use a wired communication protocol, such as an Institute of Electrical and Electronics Engineers (IEEE) 802.3 standard (which is sometimes referred to as 'Ethernet') and/or another type of wired interface. Alternatively or additionally, communication modules 112 may communicate the data or the information using a wireless communication protocol, such as: an IEEE 802.11 standard (which is sometimes referred to as 'Wi-Fi', from the Wi-Fi Alliance of Austin, Texas), Bluetooth (from the Bluetooth Special Interest Group of Kirkland, Washington), a third generation or 3G communication protocol, a fourth generation or 4G communication protocol, e.g., Long Term Evolution or LTE (from the 3rd Generation Partnership Project of Sophia Antipolis, Valbonne, France), LTE Advanced (LTE-A), a fifth generation or 5G communication protocol, other present or future developed advanced cellular communication protocol, or another type of wireless interface. For example, an IEEE 802.11 standard may include one or more of: IEEE 802.11a, IEEE 802.11b, IEEE 802.11g, IEEE 802.11-2007, IEEE 802.11n, IEEE 802.11-2012, IEEE 802.11-2016, IEEE 802.11ac, IEEE 802.11ax, IEEE 802.11ba, IEEE 802.11be, or other present or future developed IEEE 802.11 technologies.

In the described embodiments, processing a packet or a frame in a given one of computers 110 (such as computer 110-1) may include: receiving the signals with a packet or the frame; decoding/extracting the packet or the frame from the received signals to acquire the packet or the frame; and processing the packet or the frame to determine information contained in the payload of the packet or the frame. Note that the communication in FIG. 1 may be characterized by a variety of performance metrics, such as: a data rate for successful communication (which is sometimes referred to as 'throughput'), an error rate (such as a retry or resend rate), a mean squared error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization'). Note that wireless communication between components in FIG. 1 uses one or more bands of frequencies, such as: 900 MHz, 2.4 GHz, 5 GHz, 6 GHz, 60 GHz, the Citizens Broadband Radio Spectrum or CBRS (e.g., a frequency band near 3.5 GHz), and/or a band of frequencies used by LTE or another cellular-telephone communication protocol or a data communication protocol. In some embodiments, the communication between the components may use multi-user transmission (such as orthogonal frequency division multiple access or OFDMA).

Moreover, computation modules 114 may perform calculations using: one or more microprocessors, ASICs, microcontrollers, programmable-logic devices, GPUs and/or one or more digital signal processors (DSPs). Note that a given computation component is sometimes referred to as a 'computation device'.

Furthermore, memory modules 116 may access stored data or information in memory that local in computer system 100 and/or that is remotely located from computer system 100. Notably, in some embodiments, one or more of memory modules 116 may access stored measurement results in the local memory, such as dMRI data for one or more individuals (which, for multiple individuals, may include cases and controls or disease and healthy populations). Alternatively or additionally, in other embodiments, one or more memory modules 116 may access, via one or more of communication modules 112, stored measurement results in the remote memory in computer 124, e.g., via network 120 and network 122. Note that network 122 may include: the Internet and/or an intranet. In some embodiments, the measurement results are received from one or more measurement systems 126 (such as MRI scanners) via network 120 and network 122 and one or more of communication modules 112. Thus, in some embodiments at least some of the measurement results may have been received previously and may be stored in memory, while in other embodiments at least some of the measurement results may be received in real-time from the one or more measurement systems 126.

While FIG. 1 illustrates computer system 100 at a particular location, in other embodiments at least a portion of computer system 100 is implemented at more than one location. Thus, in some embodiments, computer system 100 is implemented in a centralized manner, while in other embodiments at least a portion of computer system 100 is implemented in a distributed manner. For example, in some embodiments, the one or more measurement systems 126 may include local hardware and/or software that performs at least some of the operations in the analysis techniques. This remote processing may reduce the amount of data that is communicated via network 120 and network 122. In addition, the remote processing may anonymize the measurement results that are communicated to and analyzed by computer system 100. This capability may help ensure computer system 100 is compatible and compliant with regulations, such as the Health Insurance Portability and Accountability Act, e.g., by removing or obfuscating protected health information in the measurement results.

Although we describe the computation environment shown in FIG. 1 as an example, in alternative embodiments, different numbers or types of components may be present in computer system 100. For example, some embodiments may include more or fewer components, a different component, and/or components may be combined into a single component, and/or a single component may be divided into two or more components.

As discussed previously, existing analysis techniques often suffer from a number of problems. Moreover, as described further below with reference to FIGS. 2-25, in order to address these challenges computer system 100 may perform the analysis techniques. Notably, during the analysis techniques, one or more of optional control modules 118 may divide the analysis among computers 110. Then, a given computer (such as computer 110-1) may perform at least a designated portion of the analysis. In particular, computation module 114-1 may receive (e.g., access) information (e.g., using memory module 116-1) specifying medical-imaging data that specify the central nervous system (including white matter) for one or more individuals. Note that the medical-imaging data may include or may correspond to dMRI data. Then, computation module 114-1 may perform operations in multiple stages in an analysis pipeline. For example, as described further below with reference to FIG. 4-25, the analysis pipeline may include: quality control or QC (such as visual inspection, an image resolution check and/or a gradient distribution check), skull stripping or SS, preprocessing or PP (such as denoising, motion correction and/or a correction for magnetic field inhomogeneity), harmonization (to correct for data variation, e.g., in dMRI and/or MM data, associated with different MR scanners), tissue segmentation (e.g., white matter, grey matter, tumor, cerebrospinal fluid, etc., and which may be based at least in part on structural MRI data using a convolutional neural network). The output of these portions or stages of the analysis pipeline may include tractography results (which are sometimes referred to as 'tractograms') that specify a set of neurological fibers, which are sometimes referred to as 'neural tracts' or 'streamlines'. In the present discussion, note that a 'neurological fiber' includes a sequence of three dimensional or 3D points that are connected together.

Moreover, computation module 114-1 may perform additional tractography by computing, using a predetermined (e.g., pretrained) autoencoder neural network, second tractography results that specify a second set of neurological fibers based at least in part on the tractography results and information associated with a neurological anatomical region. Note that a subset of the set of neurological fibers may be anatomically implausible and the second set of fibers may exclude the subset. Moreover, the predetermined autoencoder neural network may be trained using an unsupervised-learning technique. In some embodiments, the second set of neurological fibers may, at least in part, be different from the set of neurological fibers. Note that computing the second tractography results may include a cleaning and bundling operation in which the neurological fibers are grouped or bundled into different types of bundles of neurological fibers having different numbers of neurological fibers.

Next, computation module 114-1 may perform additional operations in multiple stages in the analysis pipeline. For example, the second tractography results may be input to or used by one or more stages or operations in the analysis pipeline, such as: statistical analysis, connectome analysis, population analysis, etc. Notably, the analysis pipeline may include: microstructure analysis, region-wise microstructure statistics (RWMS), and/or region-wise statistical analysis (RWSA). In the case of analysis for an individual, region-wise statistical analysis may be based at least in part on a comparison with a reference atlas or data structure (such as a region-wise microstructure brain atlas corresponding to multiple individuals). Alternatively, in the case of analysis of a population, at least a portion of the analysis may be computed based at least in part on cases and controls in the population.

After performing the operations in the stages in the analysis pipeline, computation module 114-1 may output a subset of a set of white-matter disease biomarkers for different neurological anatomical regions for at least the designated portion of the analysis. For a given neurological anatomical region, the set of white-matter disease biomarkers may include: an apparent fiber density, which corresponds to a total intra-axonal volume; an amount of free water; or a demyelination metric. Note that the amount of free water may correspond to neuroinflammation, and/or the apparent fiber density may correspond to axonal disruption or axonal quality. The apparent fiber density may be recovered or determined using: a diffusion fractional anisotropy (FA), water corrected fractional anisotropy, water corrected axial diffusivity, intracellular neurite orientation dispersion and density imaging (NODDI) volume fraction, and/or a local fiber orientation distribution function (fODF). Moreover, the demyelination metric may include: an inverse free-water-corrected radial diffusivity, a ratio of $T_1$ to $T_2$, a magnetization transfer ratio, or MWF. As noted previously, the MWF may be the ratio of the signal amplitudes measured in or associated with two water compartments $$MWF = \frac{MW}{(MW + EICW)},$$

where MW is the signal amplitude associated with a myelin water compartment and EICW is a signal amplitude associated with an extra-intra cellular water compartment. These signal amplitude values may be obtained via a multi-exponential function and nonlinear optimization from a series of acquired $T_2$-weighted images at different echo times (e.g., up to 48 echos). In some embodiments, the set of white-matter disease biomarkers may be computed on a per-voxel basis and/or a per-neurological-fiber (or fixel) basis.

Furthermore, as described further below with reference to FIGS. 26-35, one or more feedback modules 128 in computer system 100 may use the set of white-matter disease biomarkers for different neurological anatomical regions to provide feedback information associated with at least the individual or the population. For example, the set of white-matter disease biomarkers for different neurological anatomical regions may be inputs to a pretrained predictive model (such as a machine-learning model or a neural network), which outputs the feedback information. Note that the feedback information may include: diagnostic information, information associated with disease progression (such as a disease stage), information regarding efficacy of a treatment, or a treatment recommendation (e.g., based at least in part on the disease stage). In some embodiments, the feedback information (such as the diagnostic information) may be based at least in part on a volume of a neurological anatomical region in at least the individual, such as the hippocampus.

In these ways, computer system 100 may automatically and accurately analyze white matter for at least an individual or a population, such as: perform filtering and/or grouping or bundling of the neurological fibers, computing the set of white-matter disease biomarkers, etc. These capabilities may allow computer system 100 to perform subsequent analyses or one or more additional operations, such as: connectome analysis, white matter segmentation, one or more clinical trial enrollment or exclusion criteria, assessing the impact of a medical intervention for a disease (e.g., in a clinical trial for a candidate pharmaceutical agent, neurostimulation and/ or another type of therapy), precision medicine (such as in selecting a correct medical intervention to treat a disease, e.g., as a companion diagnostic for a prescription drug or a dose of a prescription drug), etc. For example, the more-accurate white-matter results may allow more accurate determination of: an axon density index, radial diffusion, volume, a myelin index or metric, an inflammation index or metric, fractional anisotropy (which is sensitive to anomalies), free water, apparent fiber density, a microglia index or metric, an astrocyte index or metric, an oligodendrocyte index or metric, a lesion edema index or metric, a cerebro-spinal fluid index or metric and/or, more generally, a characteristic or attribute associated with microstructure environment (e.g., on a sub-millimeter length scale that is less than a length scale corresponding to a voxel) of one or more neurological fibers (and, more generally, white matter) in particular neurological anatomic regions. Note that the disease may include: Parkinson's disease, Alzheimer's disease, multiple sclerosis, amyotrophic lateral sclerosis (ALS) or Lou Gehrig's disease, normal pressure hydrocephalus, concussion, migraine, epilepsy, a type of cancer, an autoimmune disease, schizophrenia, depression, bipolar disorder, another type of mental illness, traumatic brain injury, an alcohol-use disorder, a neurodegenerative disease, a neuroinflammatory disease, or another type of neurological disease of the central nervous system. Consequently, the analysis techniques may facilitate accurate, value-added use of the measurement results, such as medical-imaging data.

Figure 2:
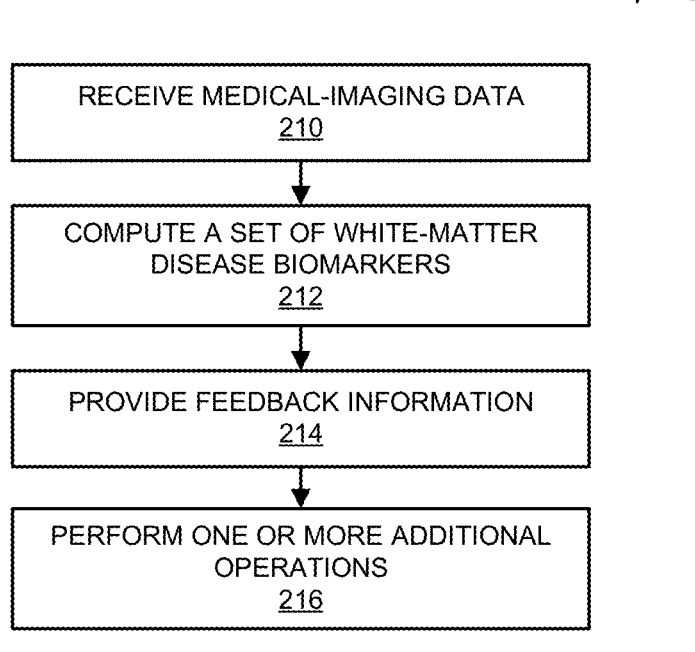
FIG. 2 is a flow diagram illustrating an example of a method for providing feedback information using a computer system in FIG. 1 in accordance with an embodiment of the present disclosure.

We now describe embodiments of the method. FIG. 2 presents a flow diagram illustrating an example of a method 200 for providing feedback information, which may be performed by a computer system (such as computer system 100 in FIG. 1). During operation, the computer system may receive medical-imaging data (operation 210) associated with at least an individual or one or more individuals. For example, the receiving may include accessing the information in memory. Note that the medical-imaging data may be associated with magnetic-resonance images of at least the individual or the one or more individuals, including: $T_1$-weighted, $T_2$-weighted, proton density, fluid-attenuated inversion recovery (FLAIR), b-value images, diffusion weighted images, diffusion tensor images, high angular resolution diffusion images, and/or another type of magnetic-resonance image or data. Thus, the medical-imaging data may include dMRI data.

Then, the computer system may compute, based at least in part on the medical-imaging data, a set of white-matter disease biomarkers (operation 212) for different neurological anatomical regions, where, for a given neurological anatomical region, the set of white-matter disease biomarkers includes an apparent fiber density, which corresponds to a total intra-axonal volume. In the present disclosure, for a voxel v and neurological fiber bundle b that goes through v, the apparent fiber density of v is the apparent proportion of its volume that is occupied by the neurological fibers of b ('apparent' because we cannot actually count the neurological fibers because they are too small). An apparent fiber density of, e.g., 0 means that no neurological fiber of b crosses that the voxel v and a value of, e.g., 1 means that v is fully occupied by the neurological fibers of b. The apparent fiber density of v may be recovered or determined using a diffusion fractional anisotropy, water corrected fractional anisotropy, water corrected axial diffusivity, intracellular NODDI volume fraction and/or a local fiber orientation distribution function. It may also be computed by considering the amplitude of the neurological fiber orientation density function (ODF) lobe aligned with b. Note that each voxel v overlapped by more than one neurological bundle may be assigned several apparent fiber density values, one for each neurological bundle.

Moreover, for the given neurological anatomical region, the set of white-matter disease biomarkers may include: an amount of free water or a demyelination metric. Note that the amount of free water may correspond to neuroinflammation, and/or the apparent fiber density may correspond to axonal disruption or axonal quality. Furthermore, the demyelination metric may include or may correspond to: an inverse free-water-corrected radial diffusivity, a ratio of $T_1$ to $T_2$, and/or a magnetization transfer ratio. Additionally, the set of white-matter disease biomarkers may be computed on a per-voxel basis and/or a per-neurological-fiber (or fixel) basis.

In the present disclosure, the amount of free water or the free-water index approximates the proportion of water contained in a voxel v of the brain. Free water may be determined from a corrected diffusion tensor imaging isotropic compartment, the isotropic fraction of NODDI and/or the isotropic compartment of any multi-compartmental diffusion MRI model. For example, we may approximate the local diffusion signal in v by the weighted sum of two tensors: a water tensor (WT) that accounts for the liquid in v, and a structural tensor or ST (which is sometimes referred to as a 'tissue tensor') that accounts for the non-liquid water-tensor tissue in v. Consequently, for v:

$$dMRI_v = \alpha \cdot W_v + (1-\alpha) \cdot ST_v,$$

where alpha is a value between, e.g., 0 and 1 which, in turn, is the free-water index.

Moreover, in the present disclosure, the demyelination metric or the myelin index (MI) measures the apparent amount of myelin contained in a voxel v. As noted previously, depending on the MRI acquisition protocol and the available modalities, the myelin index may be approximated by several measures such as the free-water corrected radial diffusivity, the $T_1/T_2$ ratio, the radial complement of the apparent fiber density, the magnetization transfer ratio or the myelin water fraction.

Next, the computer may provide the feedback information (operation 214) associated with at least the individual based at least in part on the computed set of white-matter disease biomarkers in different neurological anatomical regions. Moreover, the feedback information may include: diagnostic information, information associated with disease progression (such as a disease stage), information regarding efficacy of a treatment, or a treatment recommendation (e.g., based at least in part on the disease stage). For example, the diagnostic information may be associated with a neurological disease, including: multiple sclerosis, Alzheimer's disease, Parkinson's disease, amyotrophic lateral sclerosis, traumatic brain injury, an alcohol-use disorder, or another neurodegenerative disease. Furthermore, the feedback information may be based at least in part on a volume of a neurological anatomical region in at least the individual, such as the hippocampus.

In some embodiments, the computer system may optionally perform one or more additional operations (operation 216). For example, the medical-imaging data may be associated with a population of cases and controls, which includes at least the individual, and the feedback information may be associated with the population.

Moreover, the feedback information is determined using a pretrained predictive model. For example, the pretrained predictive model may include: a machine-learning model or a neural network. Note that a given node in a given layer in the neural network may include an activation function, and the activation function may include: a ReLU, a leaky ReLU, an ELU activation function, a parametric ReLU, a tanh activation function, or a sigmoid activation function.

Furthermore, the computer system may dynamically determine the neurological anatomical regions that are of interest based at least in part on changes (e.g., as a function of time relative to previously computed values for at least the individual) of the set of white-matter disease biomarkers and/or based at least in part on a type of disease (such as predetermined pathophysiology associated with a type of disease). Additionally, the feedback information may be based at least in part on the dynamically determined neurological anatomical regions.

In some embodiments of method 200, there may be additional or fewer operations. Furthermore, the order of the operations may be changed, and/or two or more operations may be combined into a single operation.

Figure 3:
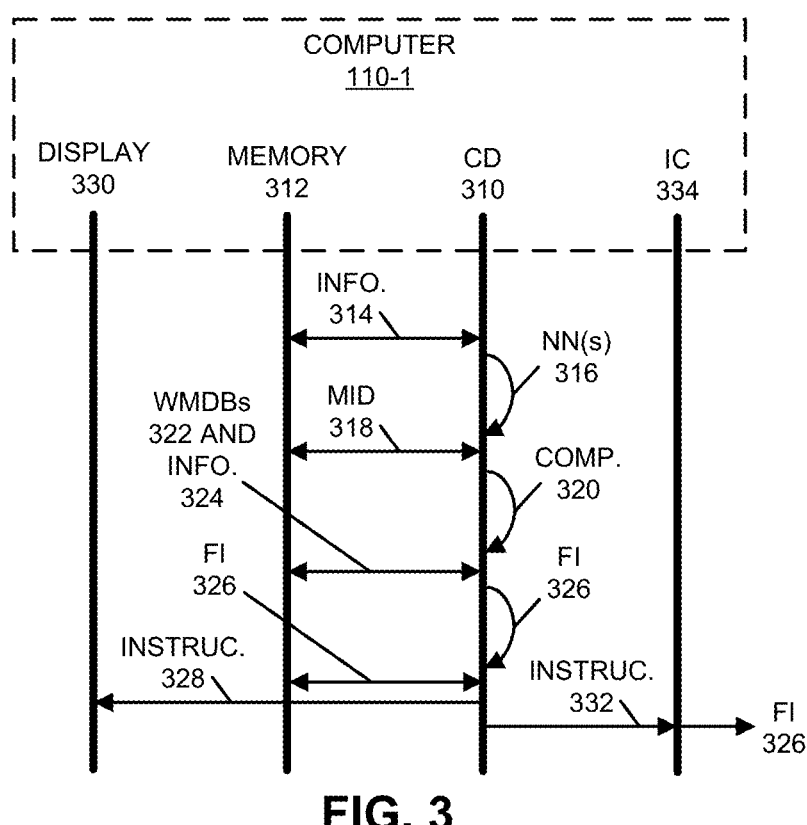
FIG. 3 is a drawing illustrating an example of communication between components in a computer system in FIG. 1 in accordance with an embodiment of the present disclosure.

Embodiments of the analysis techniques are further illustrated in FIG. 3, which presents a drawing illustrating an example of communication among components in computer system 100. In FIG. 3, a computation device (CD) 310 (such as a processor or a GPU) in computer 110-1 may access, in memory 312 in computer 110-1, information 314 specifying configuration instructions and hyperparameters for one or more predetermined or pretrained models, such as one or more neural networks (NNs) 316. After receiving the configuration instructions and the hyperparameters, computation device 310 may implement the one or more neural networks 316.

Moreover, computation device 310 may access in memory 312 information specifying medical-imaging data (MID) 318 that specify white matter for at least an individual. After receiving medical-imaging data 318, computation device 310 may compute 320, using the one or more neural networks 316 and based at least in part on the medical-imaging data 318, a set of white-matter disease biomarkers (WMDBs) 322 for different neurological anatomical regions (as specified by information 324), where, for a given neurological anatomical region, the set of white-matter disease biomarkers includes: an apparent fiber density, which corresponds to a total intra-axonal volume; an amount of free water; and/or a demyelination metric. After or while performing the computations, computation device 310 may store results, including the set of white-matter disease biomarkers 322 and information 324, in memory 312.

Next, computation device 310 may determine feedback information (FI) 326 associated with at least the individual based at least in part on the computed set of white-matter disease biomarkers 322 in different neurological anatomical regions. This feedback information may be stored in memory 312. Alternatively or additionally, computation device 310 may provide instructions 328 to a display 330 in computer 110-1 to display feedback information 326. In some embodiments, computation device 310 may provide instructions 332 to an interface circuit 334 in computer 110-1 to provide feedback information 326 to another computer or electronic device (not shown).

While FIG. 3 illustrates communication between components using unidirectional or bidirectional communication with lines having single arrows or double arrows, in general the communication in a given operation in this figure may involve unidirectional or bidirectional communication.

In some embodiments, the set of white-matter disease biomarkers includes free-water, apparent-fiber-density and myelin metrics. These white matter disease biomarkers may be used in conjunction with different neurological diseases or neurodegenerative diseases. For example, the neurological diseases may include: Alzheimer's disease, Parkinson's disease, multiple sclerosis, traumatic brain injury, depression, amyotrophic lateral sclerosis and/or chronic traumatic encephalopathy.

In the discussion that follows, Alzheimer's disease, Parkinson's disease and multiple sclerosis are used as illustrative examples. Because Alzheimer's disease, Parkinson's disease and multiple sclerosis are, in general, slowly progressing neurological diseases, they often have corresponding signatures associated with them. Notably, in their early stages, Alzheimer's disease, Parkinson's disease and multiple sclerosis are characterized by inflammation of the white matter, which typically causes the free-water metric to increase. At this stage, the diseases are often unknown to the patients and the apparent-fiber-density and myelin metrics are usually stable. However, in later disease stages, the apparent-fiber-density and myelin metrics often start to decrease, thereby showing signs of axonal loss and myelin degradation. Consequently, Alzheimer's disease, Parkinson's disease and multiple sclerosis are typically characterized by an increase of free water and, in later stages of these diseases, by a decrease of the apparent-fiber-density and myelin metrics.

During clinical trials, it is important to know if a particular medication is effective or not. Interestingly, when a medication is effective, the free water typically decreases (which indicates that there is less inflammation in the white matter). In some cases, an increase of the apparent-fiber-density and myelin metrics are also observed, which suggests that the medication has the effect of remyelinizing the white matter and rebuilding axons. It is hypothesized that this happens when patients are in the 'middle stage' of their diseases, where myelin and axons have not been irreversibly damaged.

For traumatic brain injury, immediately following brain concussion, an increase of free water is observed because of sudden neuro-inflammation and swelling. In most cases, the free water decreases after some time as the symptoms disappear. In these cases, the apparent-fiber-density and myelin metrics are stable all along. However, in some cases, the traumatic brain injury neuroinflammation becomes chronic which in turn can affect the integrity of the white matter and lead to reduction in apparent fiber density and myelin metrics.

Thus, for Alzheimer's disease, Parkinson's disease, multiple sclerosis and traumatic brain injury, there is an increase of free water followed in time by a decrease of the apparent-fiber-density and myelin metrics.

Note that where these changes occur in the brain may depend on the neurological diseases. For example, for Alzheimer's disease the changes may occur in the fornix region and in 'Alzheimer's disease bundles.' Alternatively, for Parkinson's disease the changes may occur in the substantia nigra and 'Parkinson's disease bundles.' Moreover, for multiple sclerosis the changes may occur in the vicinity of white-matter lesions and 'multiple sclerosis bundles.' Furthermore, for traumatic brain injury the changes may occur in a variety of locations in the brain, but there are some 'traumatic brain injury bundles.' Additionally, note that Alzheimer's disease, Parkinson's disease, and multiple sclerosis (but not traumatic brain injury) are often associated with an atrophy of the hippocampal volume.

Figure 4:
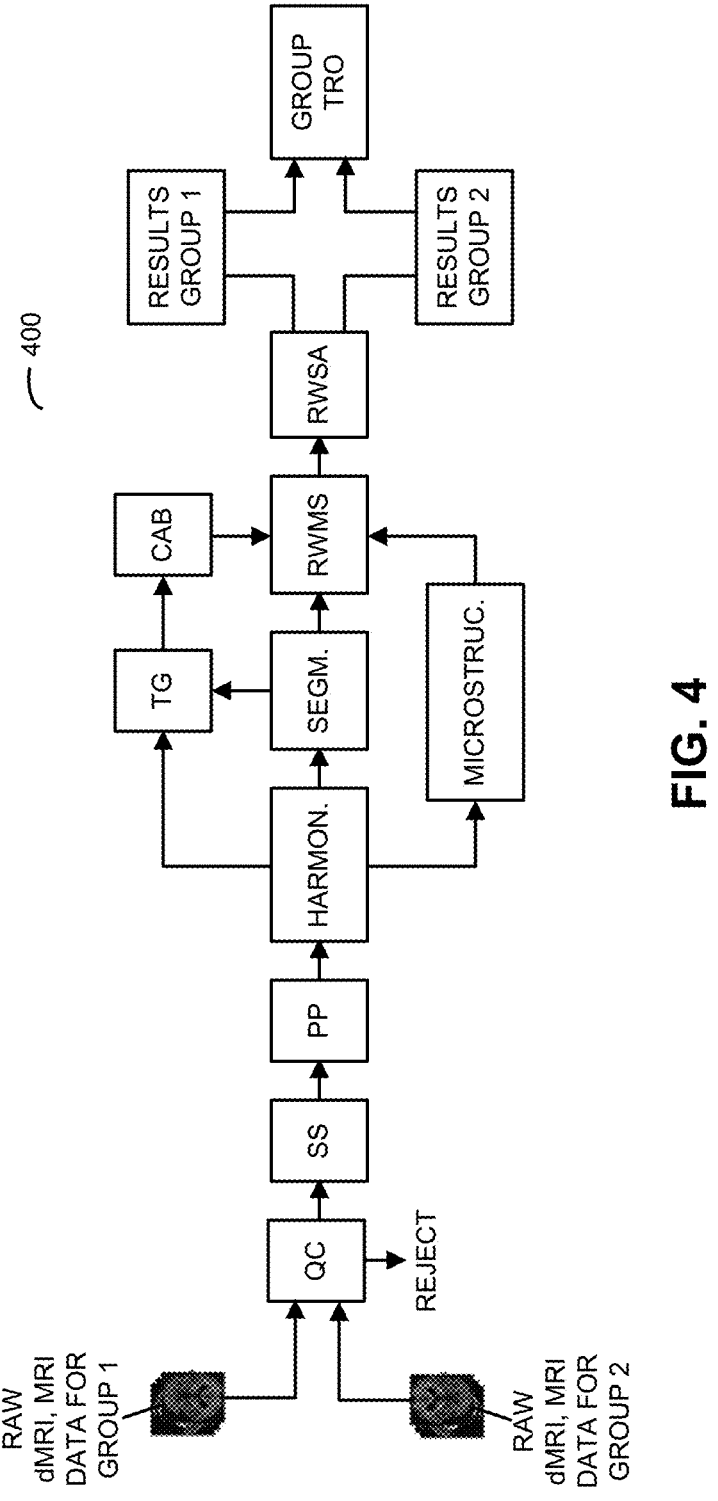
FIGS. 4-6 are drawings illustrating examples of an analysis pipeline in accordance with an embodiment of the present disclosure.
Figure 5:
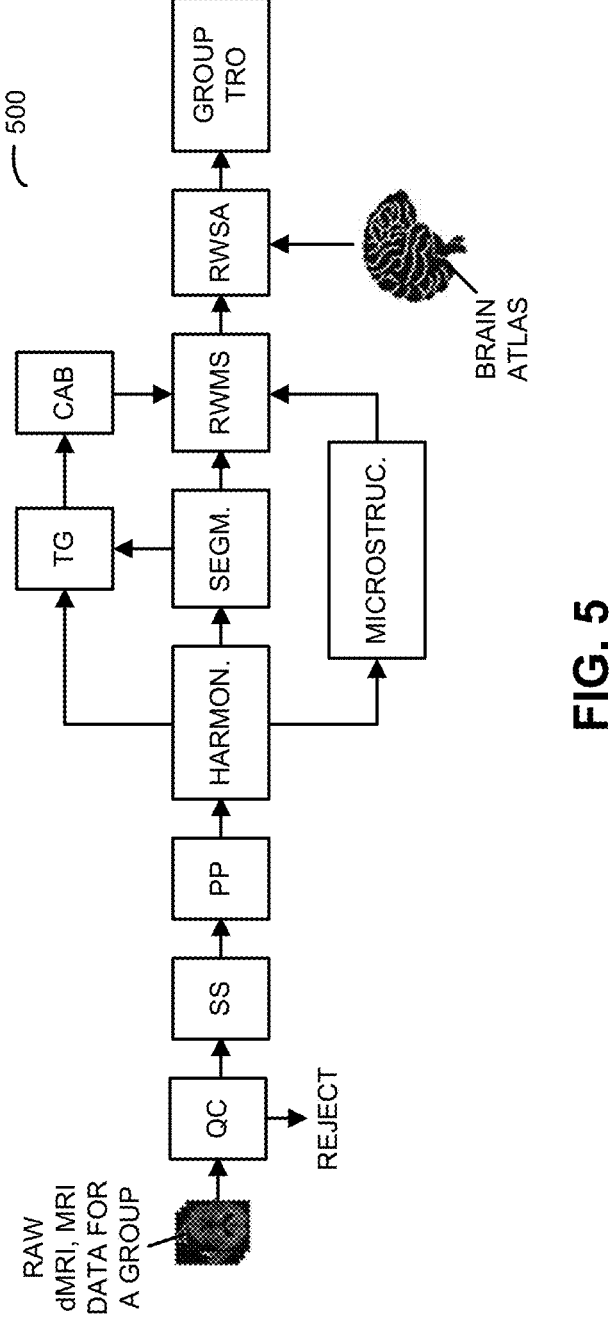
Figure 6:
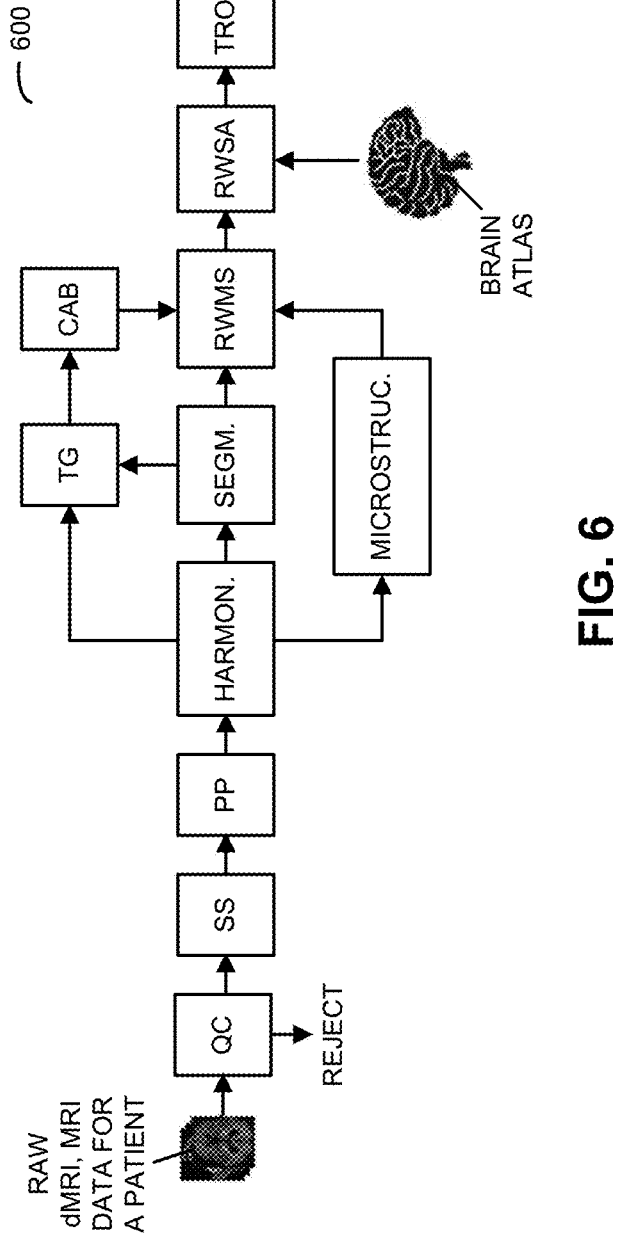

We now further describe embodiments of an analysis pipeline. FIG. 4 presents a drawing illustrating an example of an analysis pipeline 400 for use with a population, including N cases and M controls (where N and M are non-zero integers). FIG. 5 presents a drawing illustrating an example of an analysis pipeline 500 for use with a population of multiple individuals, in which comparisons are made relative to a region-wise microstructure brain atlas. FIG. 6 presents a drawing illustrating an example of an analysis pipeline 600 for use with at least an individual, in which comparisons are made relative to a region-wise microstructure brain atlas.

As discussed previously, in some embodiments the analysis pipeline may include: quality control or QC (such as visual inspection, an image resolution check and/or a gradient distribution assessment), skull stripping or SS, preprocessing or PP (such as denoising, motion correction and/or a correction for magnetic field inhomogeneity), harmonization or HARMON (to correct for data variation, e.g., in dMRI and/or MM data, associated with different MR scanners), tissue segmentation (e.g., white matter, grey matter, tumor, cerebrospinal fluid, etc., and which may be based at least in part on structural MRI data using a convolutional neural network), tractography or TG (which may be followed by a clean and bundle or CAB operation using an autoencoder neural network), microstructure analysis (which may determine fractional anisotropy, mean diffusivity, free water, etc.), region-wise microstructure statistics (RWMS), region-wise statistical analysis (RWSA), and/or a diagnostic or treatment recommendation operation or TRO (and, more generally, a feedback operation) for a group or population, or for an individual. In the case of analysis for an individual in FIG. 6, region-wise statistical analysis may be based at least in part on a comparison with a reference atlas or data structure (such as the region-wise microstructure brain atlas corresponding to multiple healthy or normal individuals, e.g., 10,000-50,000 individuals, which may be separated by gender, age, right or left handedness, etc.). Alternatively, in the case of analysis of a population, the decision or treatment recommendation operation may be computed based at least in part on cases and controls in the population (FIG. 4), or based at least in part on a comparison with a reference atlas or data structure (FIG. 5).

Note that at least some of the operations in embodiments of the pipeline are performed using pretrained models, such as machine learning models and/or neural networks. For example, at least a portion of the quality control, the skull stripping, the preprocessing, the harmonization, the tissue segmentation, the tractography and/or the diagnostic or treatment recommendation operation may be performed by corresponding pretrained models, while other operations (such as the microstructure analysis, the region-wise microstructure statistics and/or the region-wise statistical analysis) may be performed using non-machine-learning techniques (such as statistical analysis). Illustrations of architectures for several pretrained neural networks are described further below with reference to FIGS. 23-25. Note that at least some of the neural networks may be trained using labeled real images. However, in other embodiments, at least some of the neural networks may be training using synthetic or artificially generated images.

In some embodiments the analysis pipeline may be used to analyze a large amount of medical-imaging data that may have been acquired using different MRI scanners (e.g., during analysis of a population), different acquisition protocols (such as different pulse sequences) and/or at different times. For example, at least some of the medical-imaging data may be acquired using: different radio-frequency coils, different pulse sequences, different magnetic field strengths (such as 1.5 or 3T), etc. Moreover, the reconstruction techniques that are used to convert 4D measurements into real-space medical images make cause the medical images to be non-uniform or non-standardized. Consequently, there may be differences in the medical-imaging data that is input to the analysis pipeline on a per-patient basis.

Figure 7:
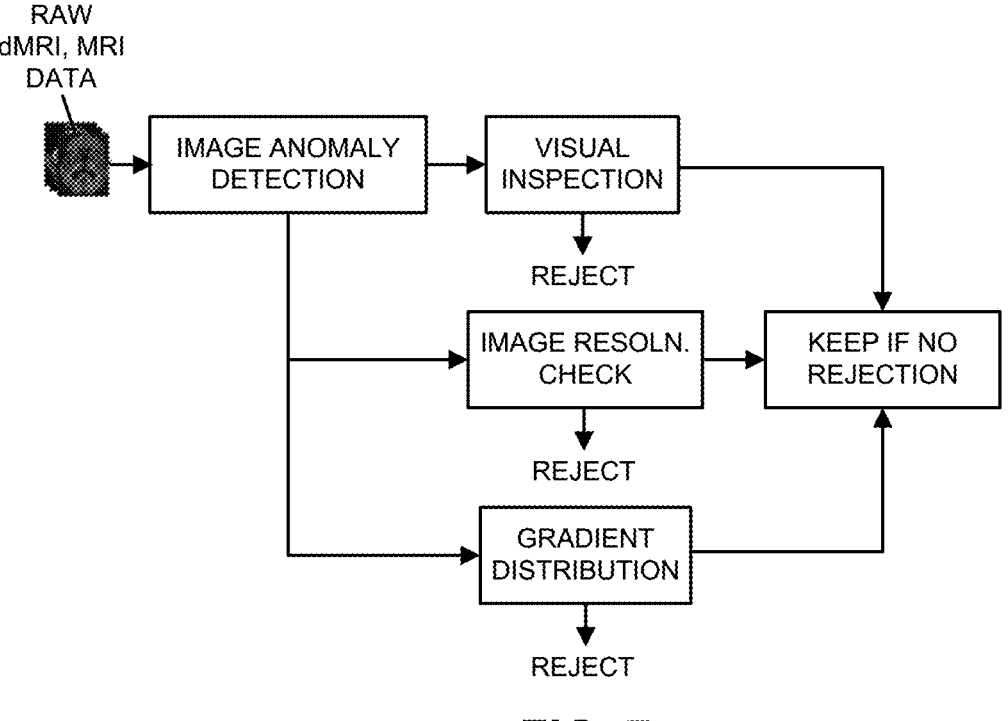
FIG. 7 is a drawing illustrating an example of quality control in an analysis pipeline in accordance with an embodiment of the present disclosure.

Therefore, as discussed previously, the analysis pipeline may include quality control to identify and/or reject medical images with artifacts (such as missing images, frame or slide drops, blurring due to motion of a given individual during the measurements, magnetic artifacts, etc.). This is shown in FIG. 7, which presents a drawing illustrating an example of quality control in an analysis pipeline. Quality control may include: an image anomaly detection followed by visual inspection; an image resolution check; and a gradient distribution assessment. The image anomaly detection may include: slice drop, magnetic artifacts, blurring, etc. Moreover, the image anomaly detection may produce a report that may be used during an optional visual inspection. Alternatively, in some embodiments the visual inspection may be automatically performed, e.g., using a pretrained model (such as a machine-learning model or a neural network). Images that include anomalies may be rejected.

Furthermore, the image resolution check may determine whether the image (voxel) resolution is, e.g., 1 mm$^3$ or 2 mm$^2$. Images with different resolution may be rejected.

Figure 8:
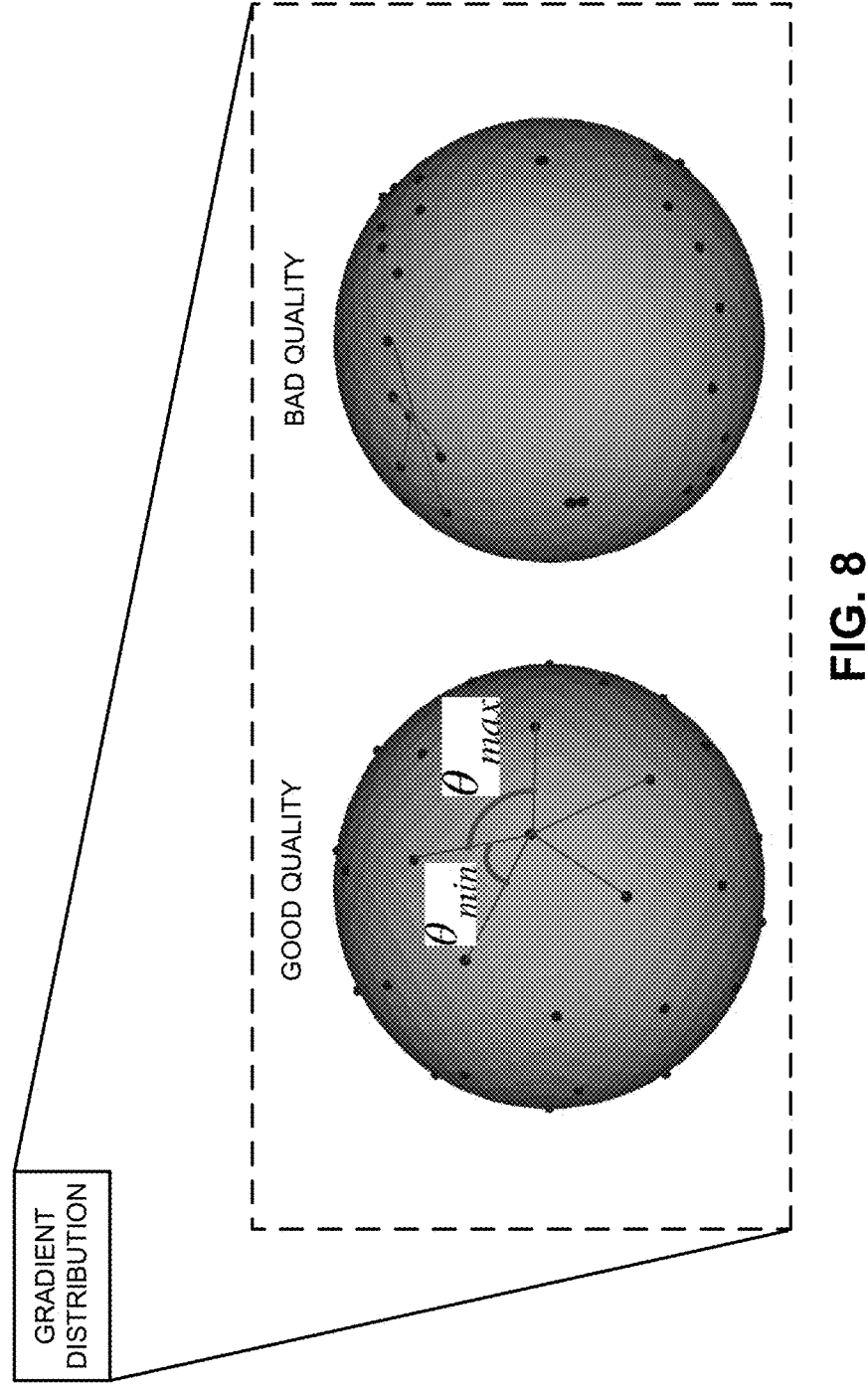
FIG. 8 is a drawing illustrating an example of determination of good versus bad quality using a gradient distribution assessment during the quality control in FIG. 7 in accordance with an embodiment of the present disclosure.

Additionally, the gradient distribution assessment may determine an angular distribution of orientation, e.g., on a sphere, which may be indicative of how freely water moves in an image. This is shown in FIG. 8, which presents a drawing illustrating an example of determination of good versus bad quality using a gradient distribution assessment during the quality control in FIG. 7. Notably, good quality may be associated with an approximately uniform angular distribution with approximately equal minimum and maximum angles, while bad quality may be associated with a narrower angular distribution with different minimum and maximum angles. Images with orientations that are nonuniform (such as with absolute differences between the minimum and maximum angle above 20°/M degrees, where M is the number of neighbors that are taken into consideration (e.g., M equals 5 in FIG. 8). In some embodiments, an angular configuration may be rejected when the local density of M nearest neighbors is twice as large as the proportion of the convex area they occupy on the sphere.

During skull stripping, the medical images may be segmented. Notably, voxels that do not correspond to or include brain tissue (such as the eyes, nose, mouth and skin) may be forced to zero. This operation may be performed using a pretrained neural network (as illustrated further below with reference to FIG. 23), which is trained using images for, e.g., 2000 individuals.

Moreover, during preprocessing, the medical images may be denoised, e.g., using a principal components technique. The preprocessing may also correct for motion of an individual during the measurement of the medical images (which can take up to an hour). For example, temporally adjacent or proximate medical images may be compared and may be regularized relative to each other. Furthermore, the preprocessing may correct for magnetic field inhomogeneity in a given MRI scanner. These magnetic field inhomogeneities may include low-frequency intensity variations present in MRI data (which are sometimes referred to as a 'bias field') that can be compensated for with a non-parametric technique that estimates the bias field and removes it from the source image (e.g. an N3 and/or an N4 bias-field correction technique). Preprocessing may also correct susceptibility artifacts. Notably, when two adjacent or proximate materials (such as bone and air) have different susceptibility, the magnetic field will have an inhomogeneous distribution that results in a local warping/distortion of the image. In some embodiments, this may be addressed using two or more acquisitions with different parameters, so that the structural content of the images may be the same but the distortions are different. From these images, an inverse transformation may be computed to compensate for these distortions. This may be performed using analysis tools, such as Topup (from the Oxford Centre for Functional MRI of the Brain, Oxford, United Kingdom) or Eddy (from the Oxford Centre for Functional MRI of the Brain, Oxford, United Kingdom).

Additionally, during harmonization, data variation in the medical images associated with different MR scanners may be performed. This may be important in embodiments where the medical images include aggregated data. Note that the harmonization may include separate operations for MRI data and dMRI data. During harmonization of MRI data, the image intensity of the images may be standardized. For example, the greyscale (0 to 1) of a given image may be globally adjusted so that the images have the same average value.

Figure 9:
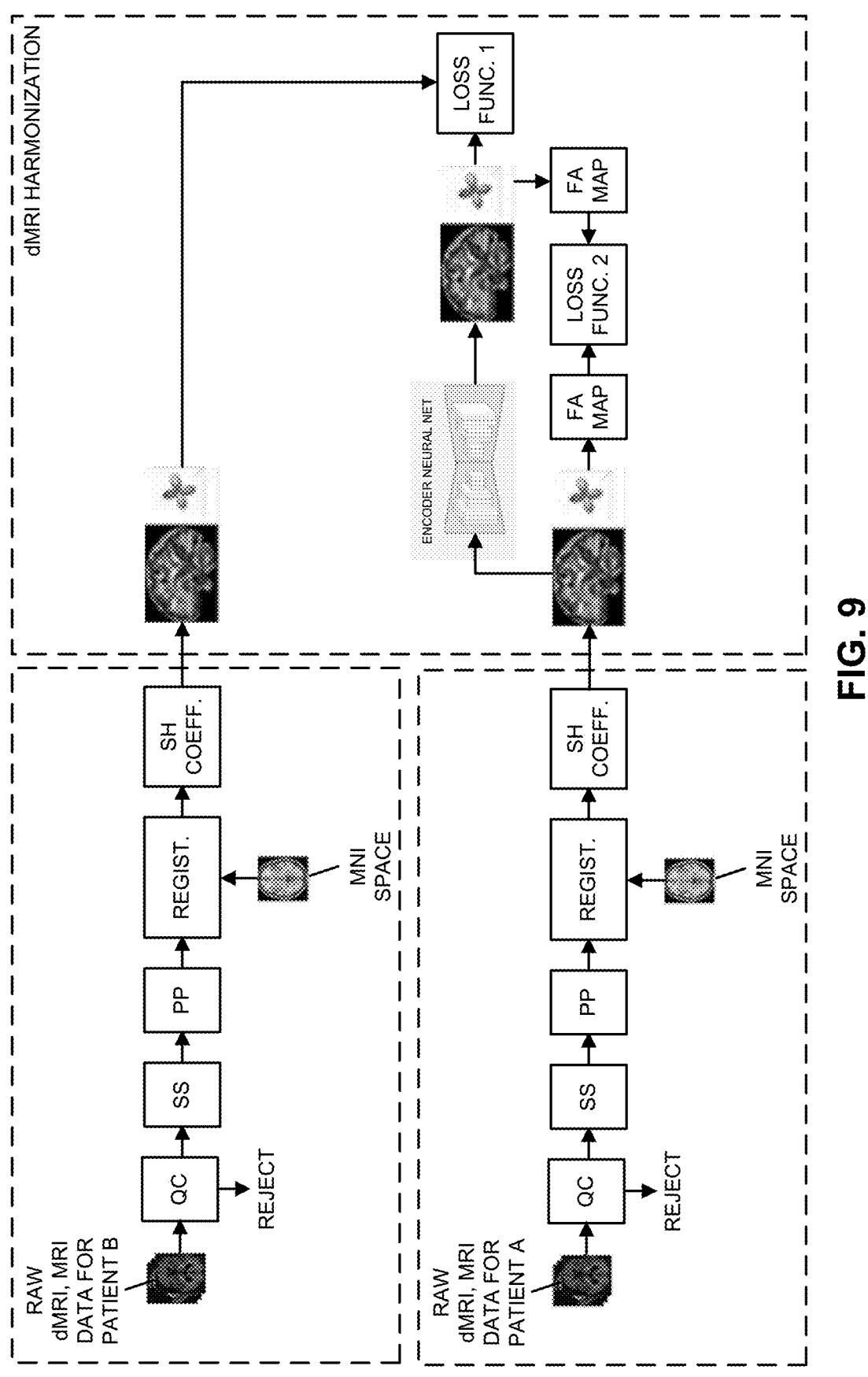
FIG. 9 is a drawing illustrating an example of self-supervised training of diffusion magnetic resonance imaging (dMRI) harmonization in an analysis pipeline in accordance with an embodiment of the present disclosure.

FIG. 9 presents a drawing illustrating an example of self-supervised training of dMRI harmonization in an analysis pipeline. Notably, after quality control, skull stripping and preprocessing, the dMRI data may be registered, e.g., using a standard brain defined by the Montreal Neurological Institute (MNI), which is referred to as an 'MNI space.' Then, spherical harmonic (SH) coefficients are determined, which summarize the signal in the dMRI data. This produces a map of glyphs of diffusion signal in the brain. The encoder/decoder neural network produces a modified homogeneous map the glyphs, which is compared to the results from another patient in loss function 1. Moreover, fraction anisotropy maps, which measure how elongated a glyph is on a per-voxel basis, are compared by loss function 2.

Note that self-supervised learning stands for learning techniques that use the raw data (and not a reference annotation) to train a model. In the embodiments illustrated in FIG. 9, the brain of a patient A is used as a target for patient B. Patient A and B can be the same person whose MRIs were acquired following different protocols or different persons sharing similar characteristics (both healthy, same age, same handedness, same gender, same education level, etc). The loss functions 1 and 2 in FIG. 9 may be a arbitrary regression loss function, such as: L1 or L2 distance, a Huber loss, a Tukey loss, etc.

Figure 10:
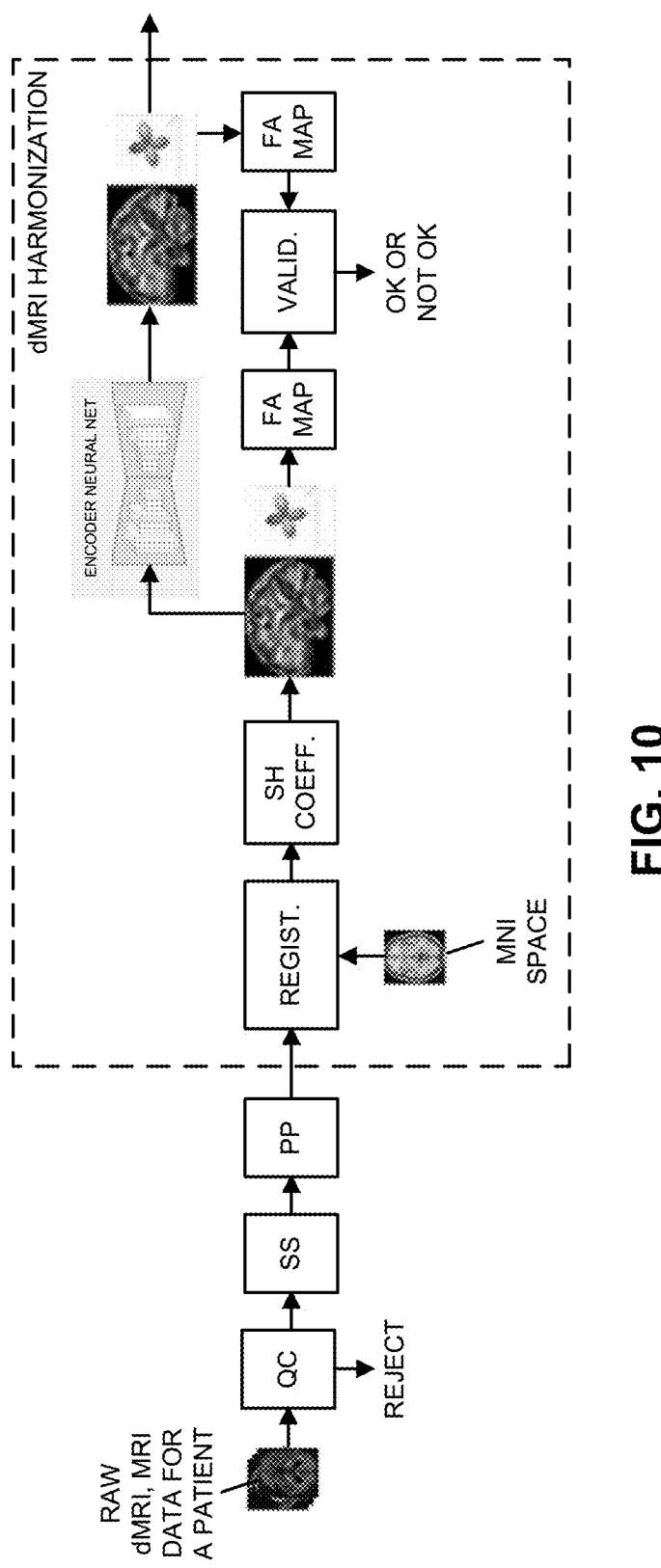
FIG. 10 is a drawing illustrating an example of diffusion magnetic resonance imaging (dMRI) harmonization in an analysis pipeline in accordance with an embodiment of the present disclosure.

After training, the resulting encoding/decoding neural network may be used to harmonize dMRI images (with reference to a neural network, such as that described further below with reference to FIG. 25, but with dMRI data at its input and output). FIG. 10 presents a drawing illustrating an example of dMRI harmonization in an analysis pipeline. Notably, the fraction anisotropy maps of the glyphs with and without processing using the encoder/decoder neural network are compared in a validation operation to determine whether or not a particular image is acceptable. The harmonization may be performed by a pretrained neural network that was trained to harmonize data. In some embodiments, acceptable criteria may include: an average difference of more than 10% in the overall white matter, and/or a local difference of more than 20%.

While harmonization can be applied to the diffusion signal (as illustrated in FIGS. 6,9 and 10), in some embodiments it may also be applied to feature maps (such as a free-water or FW map, an apparent fiber density or AFD map, a myelin map, etc.). These feature map harmonization (s) may be deep-learning based (e.g., using a pretrained neural network) or non-deep learning base (e.g., by adjusting the image histogram to a reference histogram).

Figure 11:
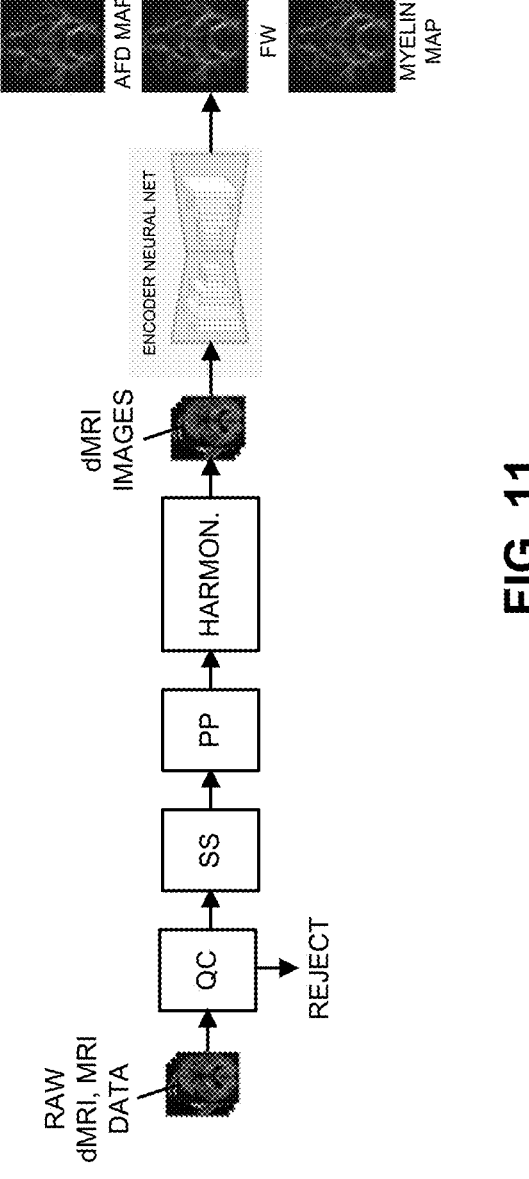
FIG. 11 is a drawing illustrating an example of conversion of low-resolution dMRI images into white-matter maps in an analysis pipeline in accordance with an embodiment of the present disclosure.

In some embodiments, the analysis pipeline may used a pretrained neural network to recover white-matter metrics (such as apparent fiber density, free water and/or a myelin index) from low-resolution dMRI data. Stated differently, this pretrained neural network may recover the white-matter metrics when we do not have the right data (e.g., sufficient data) to compute the white-matter metrics with one of the aforementioned approaches. This is shown in FIG. 11, which presents a drawing illustrating an example of conversion of low-resolution dMRI images (which include information about the apparent diffusion coefficient or ADC) into white-matter maps in an analysis pipeline. Notably, the white-matter maps may include: the apparent-fiber-density map, the free-water map, and/or the myelin map.

During tissue segmentation, white matter, grey matter, tumor, cerebrospinal fluid, a potential tumor and/or smaller regions in the brain may be segmented based at least in part on structural MRI data using a convolutional neural network. This operation may be performed using a pretrained neural network that uses a 3D convolution to generate a segmentation map (as illustrated below with reference to FIG. 24). Note that the segmentation map may be used in the tractography operation in the analysis pipeline. In some embodiments, the tissue segmentation is performed using: a U-Net neural network architecture or configuration (from the Computer Science Department at the University of Freiburg, Freiburg im Breisgau, Germany), V-Net neural network architecture or configuration (from the Computer Science Department at the University of Freiburg, Freiburg im Breisgau, Germany), E-Net (from the Faculty of Mathematics, University of Perdue, Perdue, Indiana, and/or DeepLab (from Google, Inc., Mountain View, California).

Tractography uses local orientation information from dMRI data to delineate brain white matter fiber pathways, and thus, to provide information about its structural connectivity. These connectivity pathways in tractograms are composed of streamlines virtually representing fascicles of white matter fibers. Note that the quality of the tractograms influence various aspects of connectome analysis, including: the connectivity density, the clustering degree or the existence of connections themselves, among others.

Existing tractography techniques typically face a number of challenges when propagating streamlines. For example, existing tractography techniques often have difficulty: avoiding the early termination of the tracking procedure; providing streamlines between gray matter regions that are known to be connected while avoiding spurious streamlines; ensuring the full occupancy of the white matter volume by the streamlines; and providing a complete gray matter surface coverage when streamlines reach the cortex.

Consequently, and despite the ongoing efforts to address these issues, white matter tracking techniques are often known to produce a disproportionately large number of invalid streamlines (which are sometimes referred to as 'implausible streamlines'). The category of invalid streamlines spans a broad group of streamlines that violate accepted neuroanatomical constraints attributed to fiber populations. These include streamlines that contain loops or sharp bends; streamlines that stop in non-gray matter tissues, such as the cerebrospinal fluid (CSF); streamlines that prematurely stop in the white matter; or streamlines describing trajectories between gray matter regions that are not connected structurally. Indeed, recent work indicates that, as a trade-off between sensitivity and specificity, existing tractography techniques produce a non-negligible proportion of invalid or non-existing, false-positive streamlines or connections.

To address these problems, many existing tractography techniques use filtering to detect and remove anatomically implausible streamlines, and to mitigate some of the limitations derived from current streamline propagation techniques. Notably, existing diffusion MM tractography techniques generate tractograms that may contain several million candidate streamlines representing white matter fiber populations. However, a regular tractogram including only anatomically plausible streamlines can contain in the order of 500,000 to 3,000,000 streamlines. Automatic tractography filtering of the implausible streamlines is currently based on one or more factors, including: streamline geometry features; region-of-interest-driven streamline inclusion and exclusion; clustering (which is sometimes referred to as 'bundling'); connectivity-based; and/or diffusion signal mapping or forward models.

These existing filtering approaches typically involve one or more assumptions, such as an assumed constraint. For example, invalid streamlines may be identified and removed based on: an unfeasible streamline length (and, more generally, neuroanatomical constraints); local curvature indices; streamline inclusion and exclusion criteria; and/or white matter and/or tissue local and connectivity constraints for streamline traversal. Alternatively, in clustering approaches, a similarity measure (e.g., based on assumed defined distance measure) is used to remove non-meaningful data. Moreover, in connectivity-based approaches, undesired streamlines are usually removed by imposing a regularization constraint on the tractogram-derived connectivity matrices. Furthermore, forward models often identify a subset of streamlines to be preserved in a whole-brain tractogram by, e.g., modifying a local fiber orientation distribution function (fODF) based on the diffusion signal or using local models to weigh the contribution of the diffusion signal to the streamline representation.

In principle, streamline filtering can be seen as an application of choice for deep learning classification techniques. However, neural networks are usually not easily applied to brain tractography, e.g., because of the difficulty in building a labeled dataset for use in supervised training. Indeed, finding irreproachable ground truth streamlines is typically a very difficult endeavor, with significant differences in reproducibility measures even among well-trained expert neuroanatomists. Moreover, depending on the task at hand, the labeling of the streamlines often vary considerably, and thus may require time-consuming manual verification and/or relabeling. Additionally, because existing neural network approaches are trained using supervised-learning techniques, the resulting neural networks either have a fixed number of target classes (such as a fixed number of cluster types or bundles of anatomically coherent streamlines) or use distinctly trained neural networks or models for corresponding types of clusters. Hence, regular classification neural networks are trained to predict a fixed number of classes, and thus cannot be used to predict a different set of classes without being retrained on a newly labeled set of data. These limitations constrain the flexibility of the analysis, and result in additional complexity and computational overhead, or suffer from trade-offs between accuracy and computational efficiency based on the bundle granularity.

In the analysis techniques, these problems can be addressed by using a deep autoencoder in the embodiments of the analysis pipeline for streamline-based tractography filtering (which is sometimes referred to as 'filtering in tractography using autoencoders' or FINTA). In FINTA, the autoencoder may be trained on non-curated, raw tractograms (i.e., in an unsupervised fashion or using an unsupervised-learning technique), and a filtering threshold may be computed in the learned representation space using a set of labeled streamlines. Once training is over, a resulting learned latent space may be a low-dimensional robust representation of the input streamlines, where similar streamlines are located next to each other. The filtering of plausible and implausible streamlines may then be carried out by projecting to the latent space examples of reference streamlines. Moreover, the to-be-filtered streamlines may be projected to the latent space and labeled according to a classification technique (e.g., a K nearest-neighbors technique, where K is a non-zero integer; a generative model; a Fisher discriminator; a kernel method; a decision tree; a random forest; a boosting technique, a linear perceptron; and/or a multi-layer neural network). FINTA may provide superior performance (e.g., more accurate tractograms, such as an accuracy greater than 80 or 90%; a sensitivity of greater than 80 or 90%; a precision greater than 70 or 78%; and an F1-score of greater than 70 or 80%) relative to existing tractography techniques. In addition, FINTA may be linear in terms of the streamline count at test time, thereby providing faster tractogram filtering (i.e., faster analysis). For example, FINTA may significantly reduce the computation time needed to obtain revised or improved tractography results (which are sometimes referred to as 'second tractography results') relative to existing analysis techniques (e.g., by 10×), thereby reducing the use of processor, memory and communication resources in or associated with a computer system (such as computer system 100 in FIG. 1).

Notably, in some embodiments, the autoencoder neural network may include an encoder neural network (which may be variational or not) and a decoder neural network. The output of the encoder neural network may be a so-called 'latent space'. The autoencoder neural network may have been trained on a set of neurological fibers obtained by a tractography technique on MRIs associated with one or more brains. These MRIs may be optionally registered onto a reference space (such as or similar to the Montreal Neurological Institute or MNI space). Then, the neurological fibers of a reference bundle may be input to the encoder neural network and projected into the latent space. In this way, each neurological fiber may be encoded as a 'latent vector' lying in the latent space. These latent vectors may be defined as a set A. Next, given one or more MRIs of another individual (which may or may not be registered), the tractography technique may be used to recover an associated tractogram (e.g., a set of neurological fibers). The neurological fibers in this tractogram are then input to the encoder neural network and converted into second latent vectors. These second latent vectors may be defined as a set B. Moreover, a classification technique (such as a K nearest-neighbors technique, where K is a non-zero integer; a generative model; a Fisher discriminator; a kernel method; a decision tree; a random forest; a boosting technique, a linear perceptron; and/or a multi-layer neural network) may compare set A and set B. The latent vectors in set B that are close (in a hyperdimensional latent space) to at least one latent vector in set A may be kept (i.e., included in the second tractography results), and the remaining latent vectors may be excluded or eliminated.

In some embodiments of tractography in the analysis pipeline, the computer system may compute, using a predetermined autoencoder neural network, the second tractography results that specify a second set of neurological fibers based at least in part on tractography results provided by one or more prior operations or stages in the analysis pipeline and information associated with a neurological anatomical region. Note that the predetermined autoencoder neural network may be trained using an unsupervised-learning technique. Moreover, a subset of the set of neurological fibers may be anatomically implausible and the second set of fibers may exclude the subset. For example, a latent space provided by the autoencoder may distinguish anatomically plausible and anatomically implausible neurological fibers. Furthermore, the second set of neurological fibers may, at least in part, be different from the set of neurological fibers.

For example, the predetermined auto-encoded neural network may identify different types of bundles of neurological fibers, where the different types of bundles of neurological fibers include different integer numbers of neurological fibers. Moreover, the identifying may include: discarding one or more neurological fibers in the set of neurological fibers; or classifying the one or more neurological fibers as a given type of bundle of neurological fibers that includes an integer number of neurological fibers.

Furthermore, the computing may include filtering and grouping the second set of neurological fibers from the set of neurological fibers based at least in part on the information associated with the neurological anatomical region. For example, the filtering may include classifying one or more neurological fibers as a type of bundle of neurological fibers comprising an integer number of neurological fibers.

Additionally, the computing may include: transforming (e.g., using the predetermined autoencoder) the set of neurological fibers to a latent space having a smaller number of dimensions than the set of neurological fibers; and classifying one or more neurological fibers as a type of bundle of neurological fibers that includes an integer number of neurological fibers based at least in part on a classification technique and a reference space encoded (e.g., by the predetermined autoencoder neural network) in the latent space that corresponds to the information associated with the neurological anatomical region. Note that the reference space may specify different types of bundles of neurological fibers that include different integer numbers of neurological fibers. Moreover, the classification technique may include: a K nearest-neighbors technique, where K is a non-zero integer; a generative model; a Fisher discriminator; a kernel method; a decision tree; a random forest; a boosting technique, a linear perceptron; and/or a multi-layer neural network (such as a classification neural network, e.g., one or more convolutional layers, one or more residual layers and/or one or more dense layer and/or one or more fully connected layers, which include a softmax activation function that generates an output).

In some embodiments, the computer system may sample the latent space based at least in part on a sampling technique; and generate neurological fibers in the second set of neurological fibers based at least in part on the sampled latent space. For example, the sampling technique may include: rejection sampling, a Metropolis-Hastings technique, Gibbs sampling, etc. This sampling technique may blindly sample the latent space or may be guided by a reference space or set of latent vectors. Note that the sampled latent space may result in new latent vectors, which may be input to the decoder neural network to generate new neurological fibers. These new neurological fibers may be included in or used to populate a preexisting tractogram.

Furthermore, the predetermined autoencoder neural network may include an encoder neural network (which may be variational or non-variational) and a decoder neural network, where a given neural network in the predetermined autoencoder neural network may include or combine one or more convolutional layers, one or more residual layers and one or more dense or fully connected layers. Additionally, a given node in a given layer in the given neural network may include an activation function that includes: a ReLU, a leaky ReLU, an ELU activation function, a parametric ReLU, a tanh activation function, a sigmoid activation function, and/or another type of activation function. Note that an output of the given neural network may or may not include an activation function, such as: a tanh activation function, a sigmoid activation function, an identity function, and/or another type of activation function.

Figure 12:
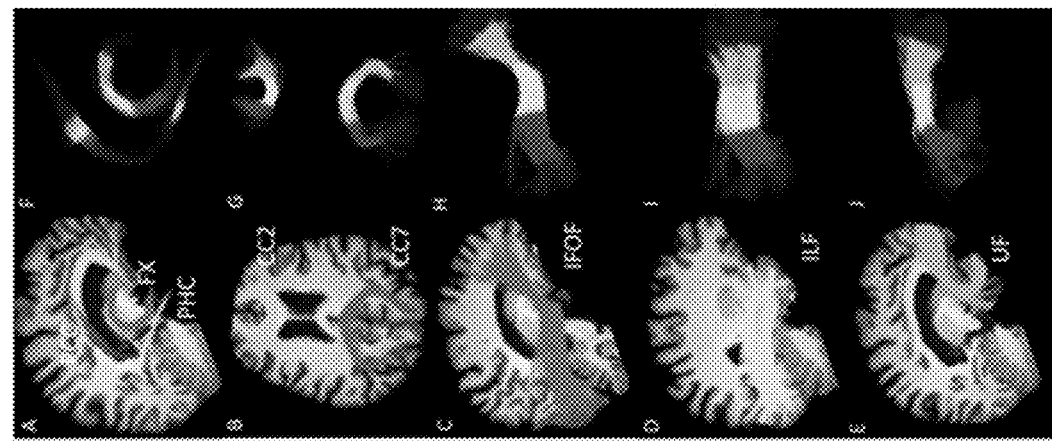
FIGS. 12-14 are drawing illustrating examples of tractography in accordance with an embodiment of the present disclosure.
Figure 12:
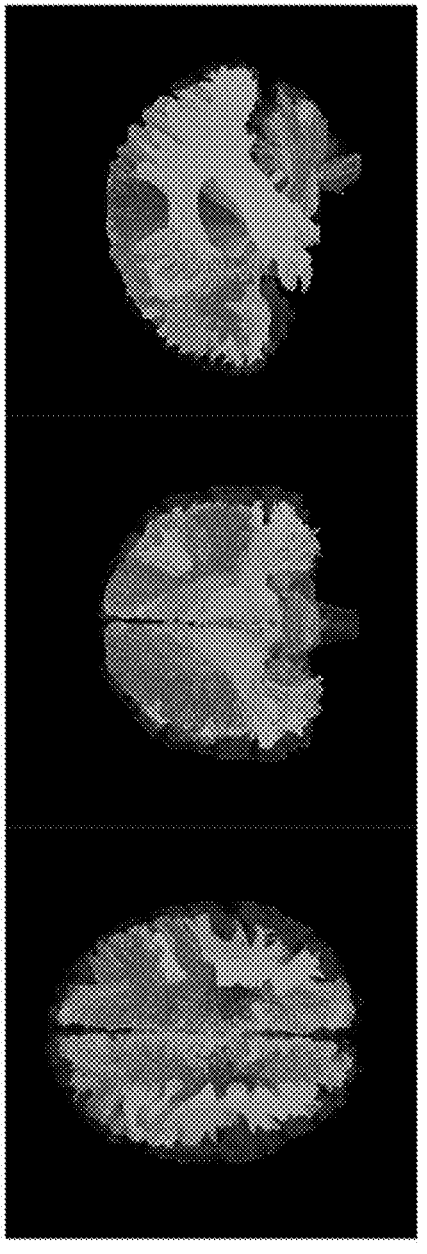
Figure 13:
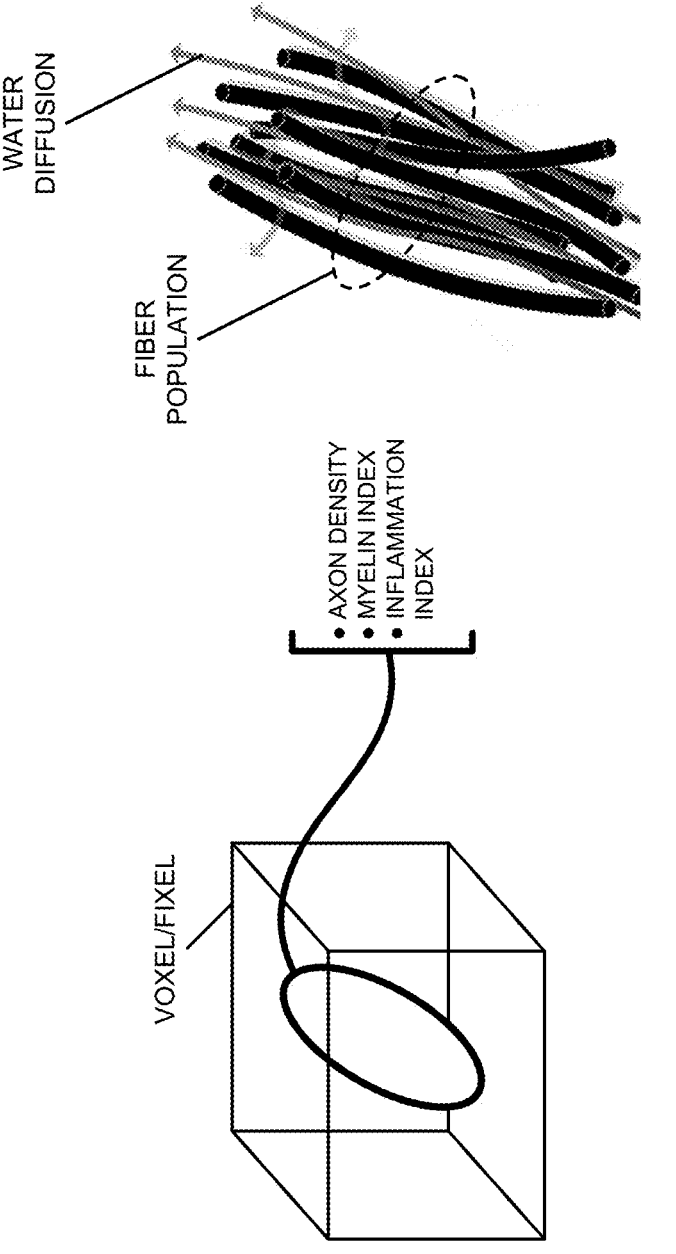
Figure 14:
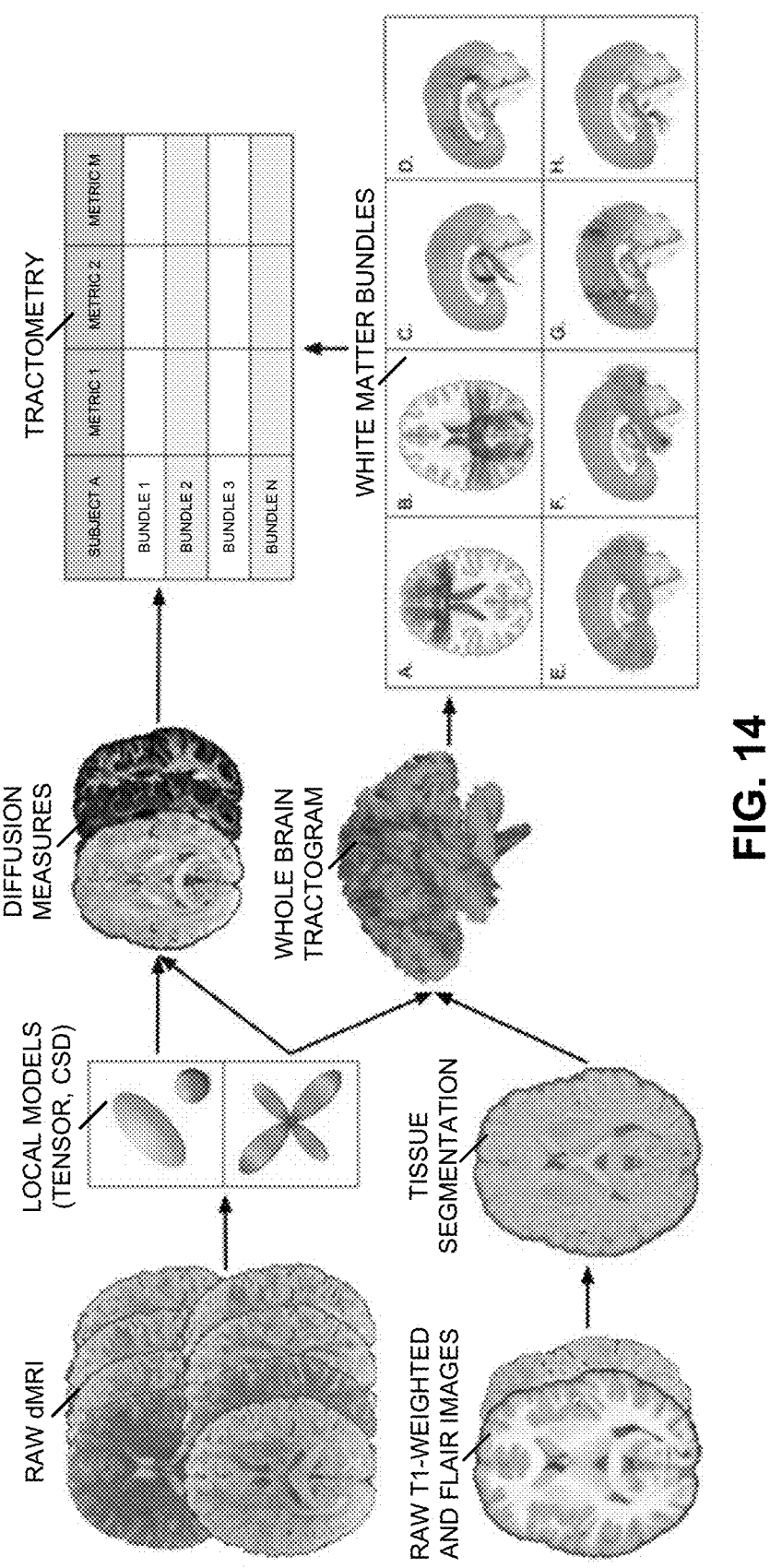
Figure 15:
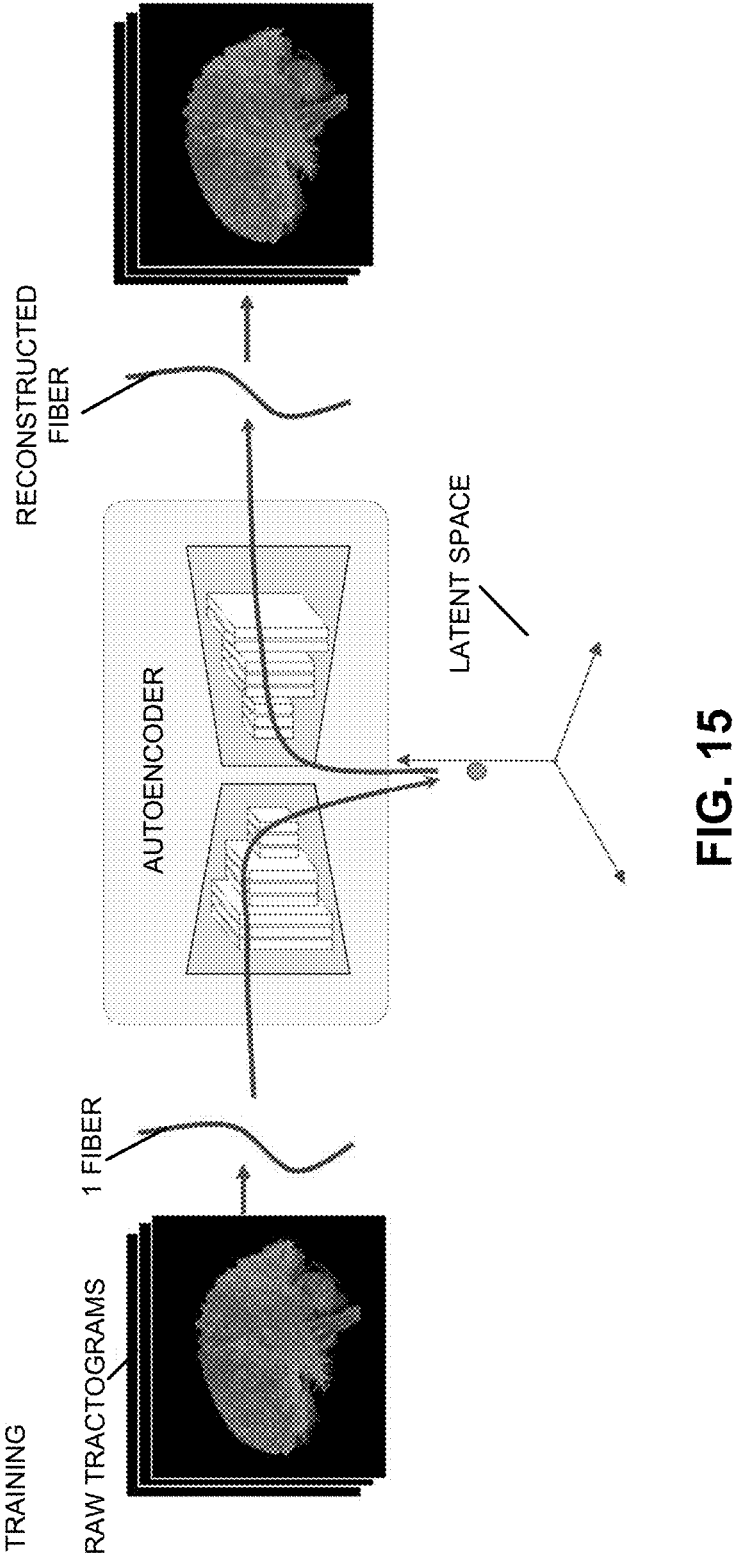

FIGS. 12-14 present drawing illustrating examples of tractography. As shown in FIG. 13, tractography may involve a track-specific tissue assessment, and accurate tractography may enable assessment of one or more attributes or characteristics associated with the microstructure environment of each fiber population (such as an axon density index, a myelin index, an inflammation index, etc.).

Autoencoder neural networks are deep neural networks that may be able to learn an efficient representation of data in an unsupervised fashion using a dimensionality reduction approach. Autoencoder neural networks may be trained to reconstruct an input signal through a series of compressing operations (known as the encoder), followed by a series of decompression operations (referred to as the decoder). As shown in FIGS. 15-21, between the encoder and the decoder there is the so-called latent space, where each point is an encoded representation of an input data sample. As discussed previously, in the analysis techniques, the input data may be a streamline, which is a sequence of three-dimensional points. Notably, a streamline may be an ordered sequence of points $s=\{c_1, c_2, \ldots, c_n\}$, where $c_i$ is a real number in a 3D space, that represents a package of similarly oriented neurological fibers describing a neural pathway within the brain white matter. A tractogram representing a set of M streamlines may be expressed as $T=\{s_1, s_2, \ldots, s_m\}$.

Autoencoder neural networks may offer advantages over other types of neural networks. First, they may be trained using raw unlabeled data, which is an asset in the context of brain tractography. Second, because the latent representation may be obtained by a series of compressing operations, two neighboring points in the latent space may correspond to input data instances that share similar characteristics. Consequently, the encoded representation may be used to redefine the notion of inter-data distance. In the context of tractography, instead of measuring the distance between two streamlines with a geometric distance function, one can project the streamlines into the latent space and measure, e.g., their Euclidean distance.

Figure 16:
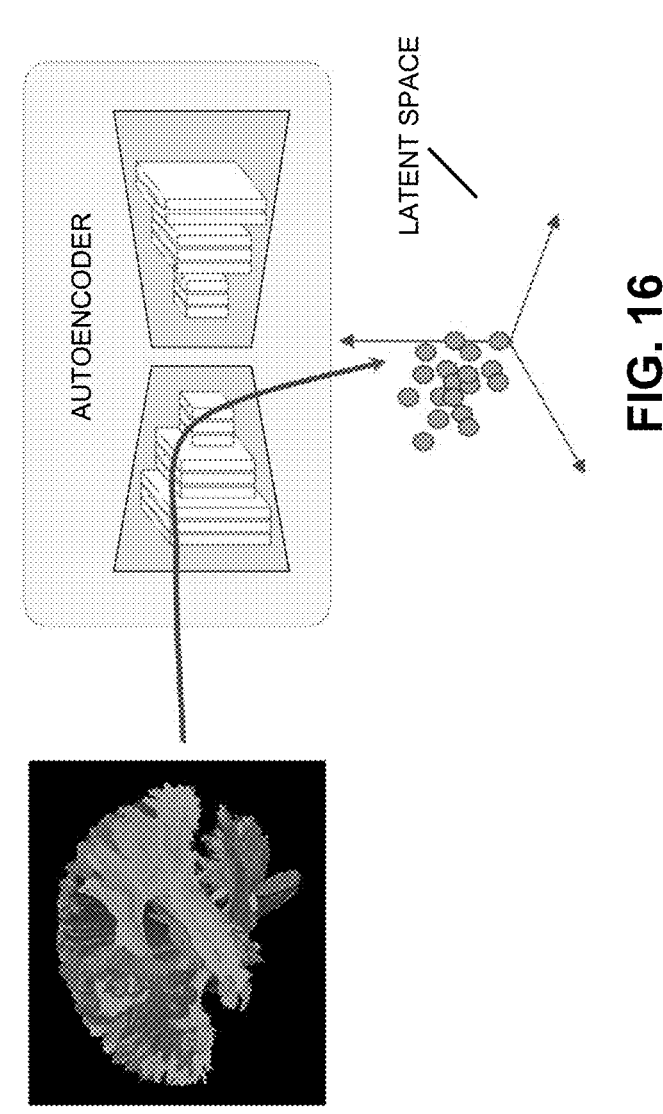
Figure 17:
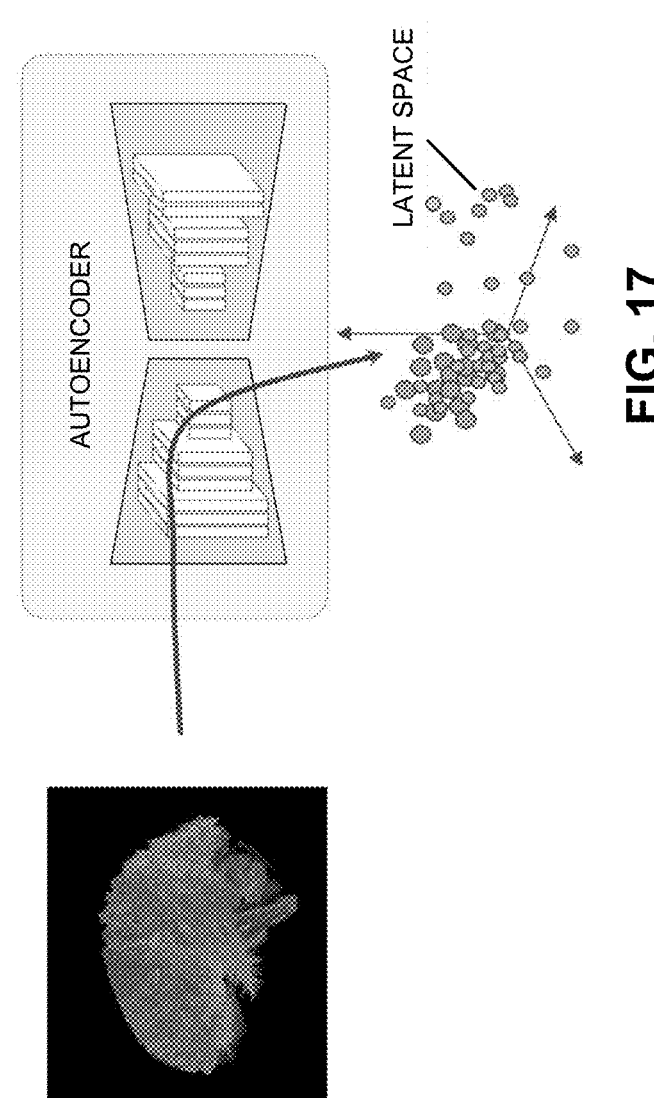
Figure 18:
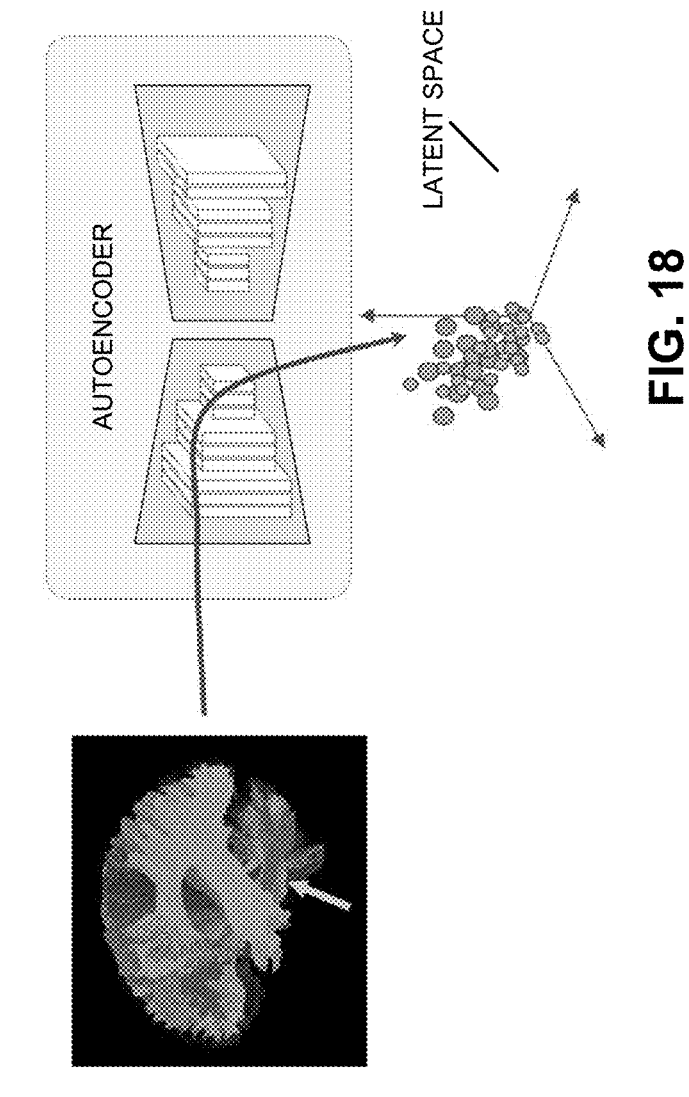
Figure 19:
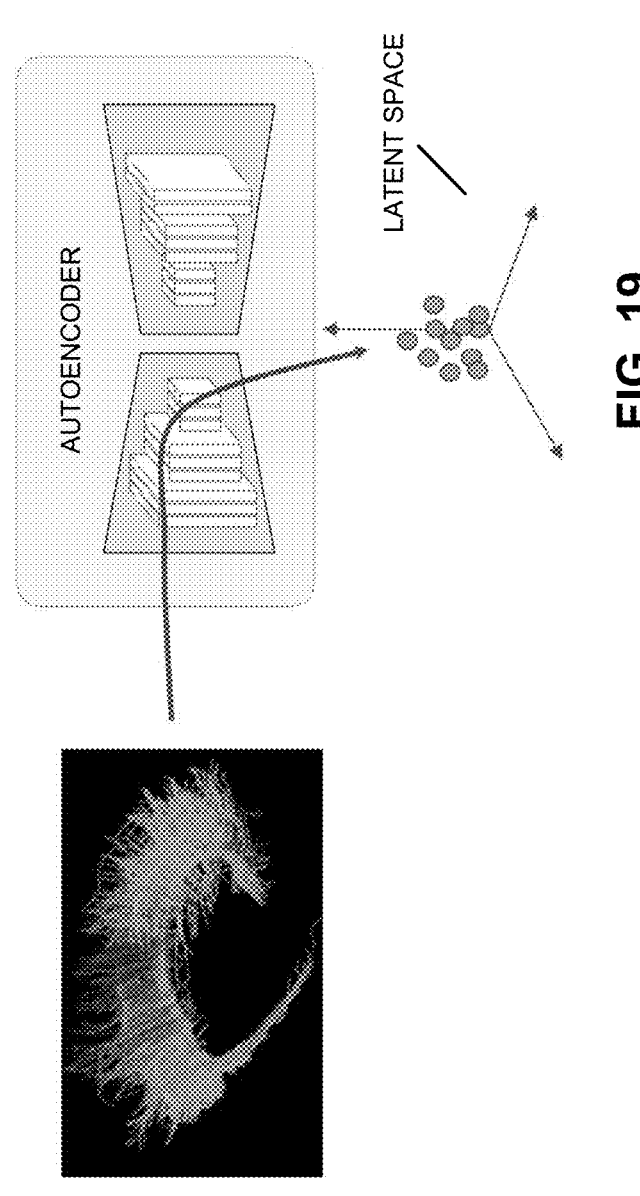
Figure 20:
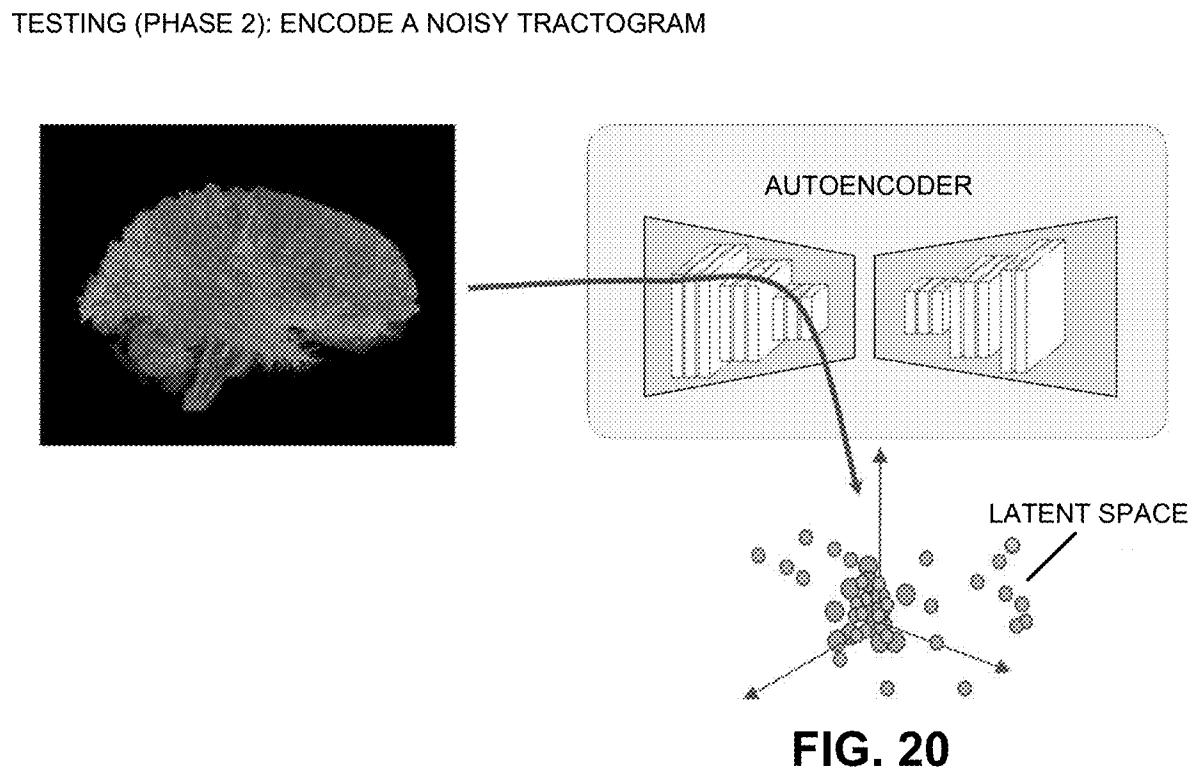
Figure 21:
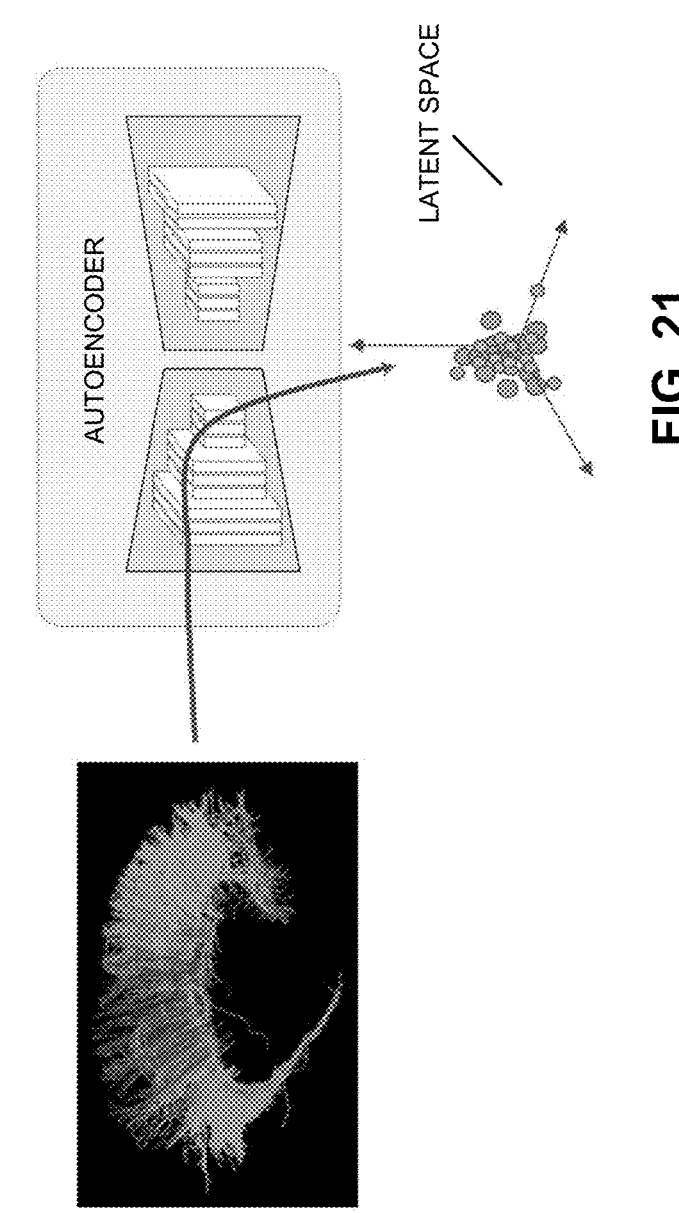

As shown in FIGS. 15-21, which present drawings illustrating examples of a cleaning and bundling operation, the disclosed analysis technique may include the following operations. First, an autoencoder neural network may be trained with a raw, uncurated tractogram. Based at least in part on the training tractogram, streamlines of interest may be labeled. These streamlines may be examples of anatomically plausible neurological fibers, streamlines representing neurological fibers belonging to predefined sets of bundles, or other streamlines that are of interest. Moreover, the streamlines may be labeled as positive streamlines. (Note that the autoencoder neural network may be trained in an unsupervised manner. However, the process of selecting the correct 'neurological' fibers, e.g., using a latent space and a nearest-neighbor technique, may use a target, such as labeled data.) Then, as shown in FIG. 16, the positive streamlines may be projected into the latent space with the encoder neural network. (In FIGS. 15-21, the latent vectors are illustrated by the circles.) Note that in case of more than two classes (such as for a multi-label bundling operation), streamlines of several classes may also be projected into the latent space. Next, as shown in FIGS. 17 and 18, given a new tractogram that is to be filtered, the streamlines of this tractogram are projected into the latent space and are labeled according to the distance to their nearest neighbor. Consequently, the filtering process in the disclosed analysis techniques may take place in the latent space.

In some embodiments, the nearest-neighbor discrimination may employ a latent-space distance cut-off value (which is sometimes referred to as a 'filtering threshold') relative to a (labeled) reference set of streamlines to discriminate the uncurated streamlines of a tractogram. The filtering threshold may represent a minimum distance at which a streamline is considered to be implausible, and its value may be computed on the separate reference set of streamlines. For example, the filtering threshold may be determined from an optimal point in a receiver operating characteristic (ROC) curve that evenly rewards true positives and penalizes false positives. Alternatively, the filtering threshold may be determined using data from a variety of tracking settings (e.g., probabilistic, deterministic, global, etc.) and datasets. Note that the filtering threshold may be, e.g., 6.568 or 13.634. However, in general the filtering threshold may be tailored or selected for a particular dataset being analyzed.

Moreover, the autoencoder neural network may be a fully convolutional neural network whose overall structure is summarized in Table 1. This autoencoder neural network may accept a streamline at its input. Because raw streamlines have a different number of vertices (long streamlines have more vertices than shorter ones), in the analysis techniques streamlines may be resampled so that they have an equal number of vertices (e.g. 256 in Table 1). Note that the latent space length may be fixed at, e.g., a value smaller than 512, such as 32. However, other values may be used.

TABLE 1

| Part | Type | Features | Size |
|---|---|---|---|
| Input | | | 3; 256 |
| Encoder | 1D convolution | 32 | 256 |
| | 1D convolution | 64 | 128 |
| | 1D convolution | 128 | 64 |
| | 1D convolution | 256 | 32 |
| | 1D convolution | 512 | 16 |
| | 1D convolution | 1024 | 8 |
| Latent Space | Fully Connected | 32 | |
| Decoder | Upsampling + 1D convolution | 1024 | 8 |
| | Upsampling + 1D convolution | 512 | 16 |
| | Upsampling + 1D convolution | 256 | 32 |
| | Upsampling + 1D convolution | 128 | 64 |
| | Upsampling + 1D convolution | 64 | 128 |
| | Upsampling + 1D convolution | 32 | 256 |
| Output | | | 3; 256 |

Furthermore, the autoencoder may be trained with an Adam optimizer with a mean squared-error loss. The hyperparameters may be adjusted using a Bayesian search technique. The learning rate of the optimizer may be fixed to a value of $6.68 \times 10^{-4}$, and weight decaying regularization with a 0.13 valued parameter may be used. Note that Table 1 provides an example of an autoencoder neural network structure. The encoder neural network may use strides of size 2, and the decoder neural network may use strides of size 1. Additionally, the upsampling stages in the decoder neural network may use an upsampling factor of 2. The autoencoder neural network may use ReLU activations throughout its convolutional layers.

Note that latent space of the autoencoder neural network may allow the streamline pair-wise distance to be reinterpreted. Notably, the analysis techniques may use the Euclidean distance between the latent representation of two streamlines as a proxy to measure their structural similarity. However, in other embodiments, a different similarity metric may be used, such as a Manhattan distance.

Figure 22:
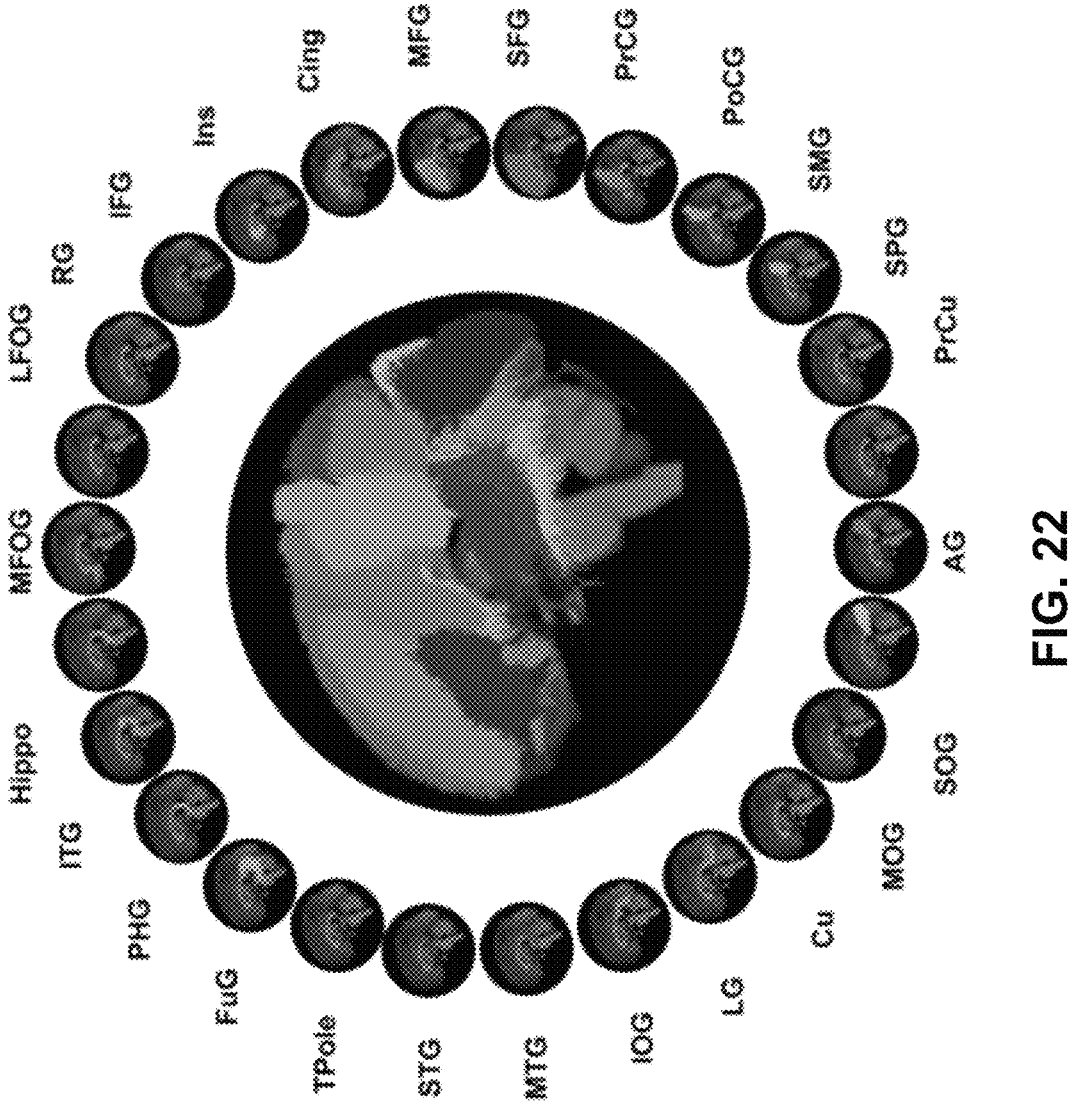
FIG. 22 is a drawing illustrating an example of bundling results in different neurological anatomical regions in accordance with an embodiment of the present disclosure.

FIG. 22 presents a drawing illustrating an example of bundling results in different neurological anatomical regions.

In contrast with existing filtering techniques that assume that the estimated streamline population at every voxel is proportionally supported by the diffusion data, the disclosed autoencoder neural network may work on tracking data only. This may make the tractography analysis techniques less sensitive to or immune against domain adaptation issues. Furthermore, in comparison with a quadratic or super-quadratic complexity of some existing filtering techniques, the disclosed tractography analysis techniques may be linear in terms of the streamline count at test time.

Additionally, compared to other deep learning techniques that may be specifically oriented to classification tasks (e.g., regular classification convolutional neural networks), the disclosed tractography analysis techniques may provide the benefit of using an unsupervised learning approach. Thus, the disclosed tractography analysis techniques may not depend on the number of classes in the input data as the output of the network does not look for maximizing the probability of a given class among the possible ones. Consequently, the disclosed tractography analysis techniques may be better suited to the reality of tractography, where there is a limited knowledge about the ground truth, and where the analysis may lend itself to different organizational levels and, thus, different classification degrees. Therefore, the disclosed tractography analysis techniques may naturally adapt to new sets of classes without the need of having to retrain the autoencoder neural network.

A potential side-benefit of the disclosed tractography analysis techniques is that the reconstructed streamlines describe a locally smooth (yet 'denoised') trajectory. Succeeding analysis pipeline or visualization processes may benefit from this attribute, thereby providing a less complicated or a more realistic long-range apparent fiber trajectory representation.

In some embodiments, downstream tractography tasks may benefit from filtering strategies applied at earlier stages when performed in a coherent manner. For example, one of such tasks is the structural connectivity analysis (or connectomics). Because the disclosed tractography analysis techniques more accurately reject implausible streamlines, they may preserve the existing connectivity. Consequently, the disclosed tractography analysis techniques may regenerate the connectome to a high degree of accuracy.

Moreover, the disclosed tractography analysis techniques may be robust across a varying spectrum of settings. The disclosed tractography analysis techniques assume that, provided that the implausible streamlines have overall distinctive features from the plausible ones, they may be cast to different regions in the latent space, and thus the filtering framework may be able to separate them, regardless of their location and arrangement in the native space or within-fascicle balance. Similarly, the autoencoder neural network may have the ability to disentangle a varying number of bundles or streamline groups. Note that the disclosed tractography analysis techniques may be used with datasets having a wide range of values for a ratio of plausible streamlines to implausible streamlines, such as between 5-70.

Continuing the discussion of the analysis technique, during the microstructure analysis, information at a sub-millimeter resolution (and, thus, less than 1 $mm^3$ voxel) may be determined, such as: fractional anisotropy, free water, etc. For example, information may be inferred at a higher resolution from lower-resolution measurements by solving an inverse nonlinear problem to determine parameters in or associated with the voxels. In some embodiments, the microstructure analysis may determine an index or a metric that reflects changes to: myelined axons, microglia, astrocytes, lesion edema, cerebrospinal fluid, a characteristic or attribute associated with microstructure environment, etc. In some embodiments, the microstructure analysis may use: diffusion tensor imaging, diffusion component imaging and/or diffusion-basis spectrum imaging.

Moreover, during the region-wise microstructure statistics analysis, microstructure maps in multiple images (such as more than five images) may be used to determine statistics for neurological anatomical regions (e.g., relative to controls in a brain atlas) for parameters, such as apparent fiber density, free water, etc. (which may include one or more biomarkers in a set of white-matter disease biomarkers). In some embodiments, the region-wise microstructure statistics may be computed using a histogram or a fit to a distribution (such as a chi-square distribution, a Student's t-distribution, a Gaussian distribution, etc.) of correlations between different regions. Note that the region-wise microstructure statistics may specify or indicate pathology, such as: disease, disease progression, risk for disease or disease progression, latency of disease, etc. As shown in FIG. 22, in some embodiments the neurological anatomical regions may include predefined neurological anatomical regions associated with functional regions in grey matter.

Furthermore, during the region-wise statistical analysis, analysis may be performed using the statistics for one or more parameters or indexes in one or more different neurological anatomical regions to compute one or more aggregate indexes or metrics (such as one or more biomarkers in a set of white-matter disease biomarkers). Note that this analysis may be performed using a predefined model, such as a machine-learning model (with one or more thresholds) or a neural network.

Additionally, as described further below with reference to FIGS. 26-35, the determined indexes, metrics and/or statistics (such as the set of white-matter disease biomarkers) may be used on the diagnostic or treatment recommendation operation or TRO (and, more generally, a feedback operation) for a group or population or for an individual.

As discussed previously, in some embodiments the computer system may use an analysis model that is pretrained or predetermined using a machine-learning technique (such as a supervised learning technique, an unsupervised learning technique and/or a neural network) and a training dataset. For example, the analysis model may include a classifier or a regression model that was trained using: a support vector machine technique, a classification and regression tree technique, logistic regression, LASSO, linear regression, a neural network technique (such as a convolutional neural network technique, an autoencoder neural network or another type of neural network technique) and/or another linear or nonlinear supervised-learning technique.

Figure 23:
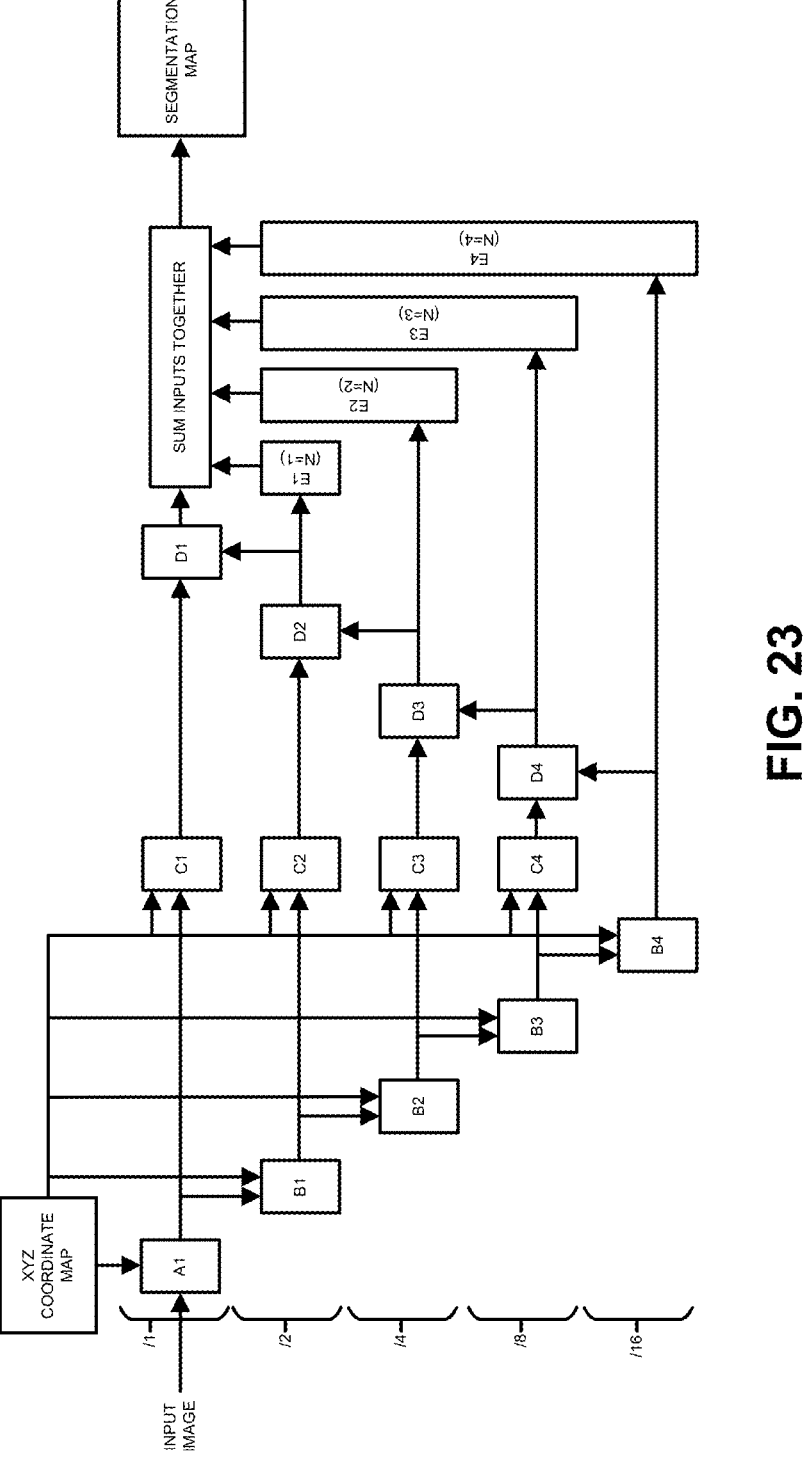
FIG. 23 is a drawing illustrating an example of a skull stripping neural network configuration in an analysis pipeline in accordance with an embodiment of the present disclosure.

For example, FIG. 23 presents a drawing illustrating an example of a skull stripping neural network configuration in an analysis pipeline. In FIG. 23, A1 represents a 3D convolution operation, followed by an instance normalization operation, followed by leaky ReLU operation, followed by a 3D convolution operation, followed by an instance normalization operation, and then followed by a leaky ReLU operation. Moreover, B1-4 represent instances of a 3D convolution of size/2 operation, followed by an instance normalization operation, followed by leaky ReLU operation, followed by a 3D convolution operation, followed by an instance normalization operation, and then followed by a leaky ReLU operation. Furthermore, C1-4 represent instances of a 3D convolution operation, followed by an instance normalization operation, followed by leaky ReLU operation, followed by a 3D convolution operation, followed by an instance normalization operation, and then followed by a leaky ReLU operation. Additionally, D1-4 represent instances of a 3D convolution transpose of size 2× operation, followed by a feature maps concatenation and a 3D convolution operation, followed by an instance normalization operation, a leaky ReLU operation, followed by a 3D convolution operation, followed by an instance normalization operation, and then followed by a leaky ReLU operation. E1-4 represent instances of a 3D convolution operation, and then followed by a 3D convolution transpose operation (repeated N times). Note that in FIG. 23 the loss function may include: cross-entropy, a dice score and regularization.

Figure 24:
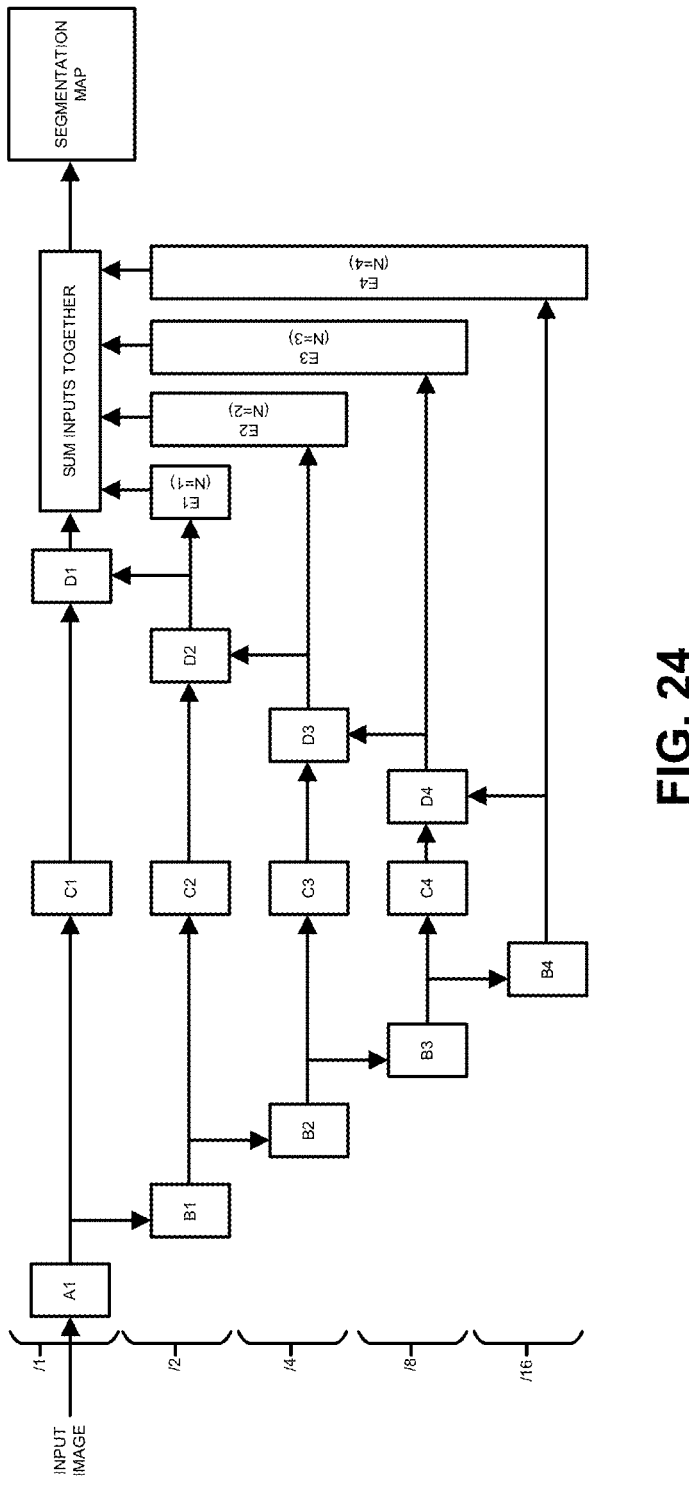
FIG. 24 is a drawing illustrating an example of a structural MRI segmentation neural network configuration in an analysis pipeline in accordance with an embodiment of the present disclosure.

Moreover, FIG. 24 presents a drawing illustrating an example of a structural MRI segmentation neural network configuration. In FIG. 24, A1 represents a 3D convolution operation, followed by an instance normalization operation, followed by leaky ReLU operation, followed by a 3D convolution operation, followed by an instance normalization operation, and then followed by a leaky ReLU operation. Moreover, B1-4 represent instances of a 3D convolution of size/2 operation, followed by an instance normalization operation, followed by leaky ReLU operation, followed by a 3D convolution operation, followed by an instance normalization operation, and then followed by a leaky ReLU operation. Furthermore, C1-4 represent instances of a 3D convolution operation, followed by an instance normalization operation, followed by leaky ReLU operation, followed by a 3D convolution operation, followed by an instance normalization operation, and then followed by a leaky ReLU operation. Additionally, D1-4 represent instances of: a 3D convolution transpose of size 2× operation; or a 3D convolution transpose of size 2× operation, followed by a feature maps concatenation and a 3D convolution operation, followed by an instance normalization operation, a leaky ReLU operation, followed by a 3D convolution operation, an instance normalization operation, and then followed by a leaky ReLU operation. E1-4 represent instances of a 3D convolution operation, and then followed by a 3D convolution transpose operation (repeated N times). Note that in FIG. 24 the loss function may include: cross-entropy, a dice score, a focal loss and regularization.

Figure 25:
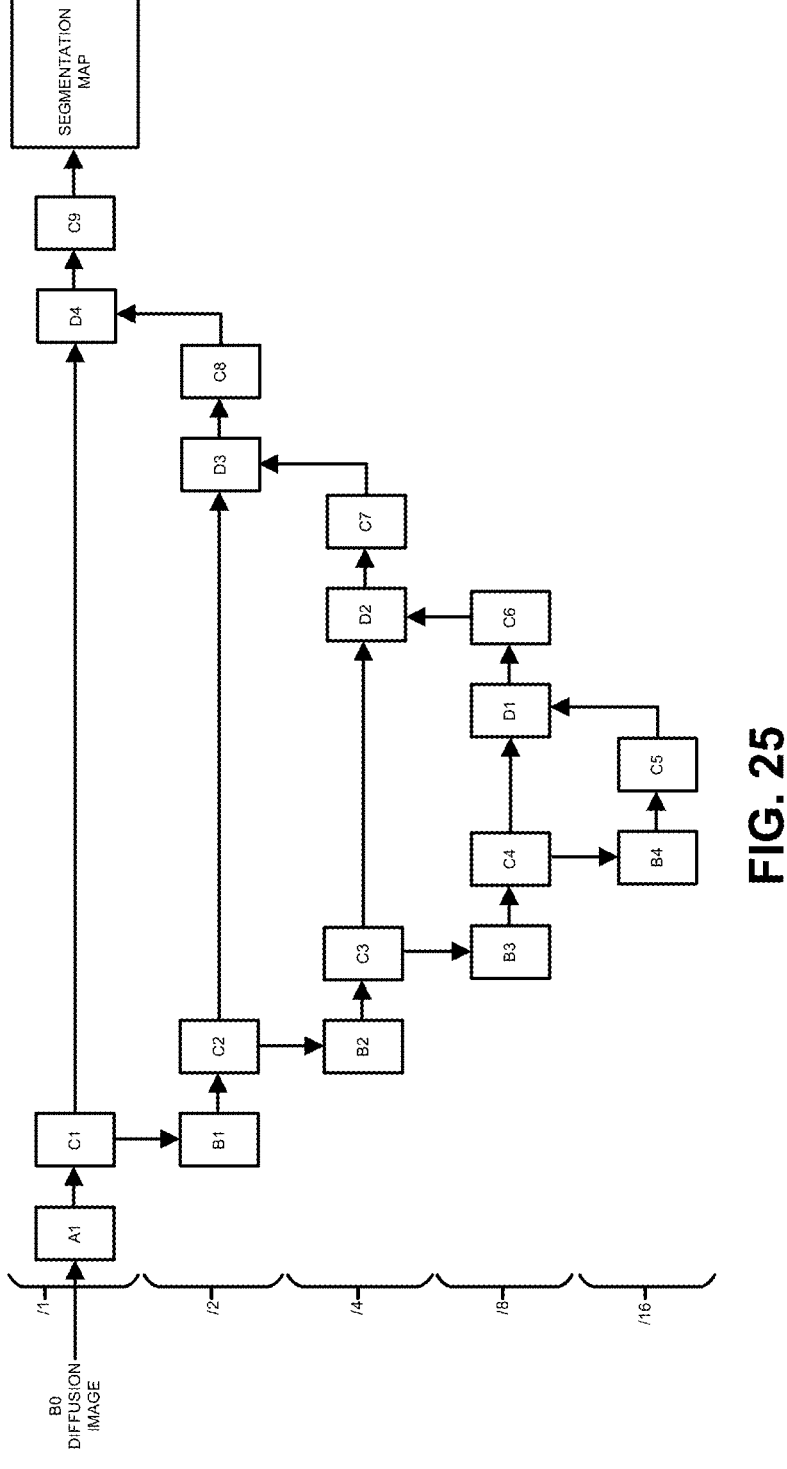
FIG. 25 is a drawing illustrating an example of a dMRI segmentation neural network configuration in an analysis pipeline in accordance with an embodiment of the present disclosure.

Furthermore, FIG. 25 presents a drawing illustrating an example of a dMRI segmentation neural network configuration in an analysis pipeline. In FIG. 25, A1 represents a 3D convolution operation, and then followed by a ReLU operation. Moreover, B1-4 represent instances of a 3D convolution of size/2 operation, and then followed by a ReLU operation. Furthermore, C1-9 represent instances of a four-layer dense block (which may include a neural network module that connects several convolution layers, e.g., 4 to 6, with each other via a series of feature map concatenation operations). Additionally, D1-4 represent instances of: a 3D convolution transpose of size 2× operation; or a 3D convolution transpose of size 2× operation, followed by a ReLU operation, followed by a feature maps concatenation and a 3D convolution operation, and then followed by a ReLU operation. Note that in FIG. 25 the loss function may include: cross-entropy, a dice score and regularization.

We now describe the set of white-matter disease biomarkers and there use in conjunction with diagnosis, monitoring and treatment Alzheimer's disease, which is used as an illustrative example. However, these analysis techniques may be used with a wide variety of diseases.

Alzheimer's disease is usually associated with grey matter (GW), including: memory loss, brain atrophy and, more recently, loss of hippocampus volume, which is the memory center of the brain. However, very little attention has been given to white matter (WM) in Alzheimer's disease progression, both in academia and industry. This is, at least in part, a result of technological barriers to imaging and quantifying white matter, in animal models and humans. With recent advances in imaging technology (such as in microscopy, MRI, PET, etc.), and especially DMRI, it is now possible to quantify white-matter microstructure and its deterioration due to a neurodegenerative disease.

Figure 26:
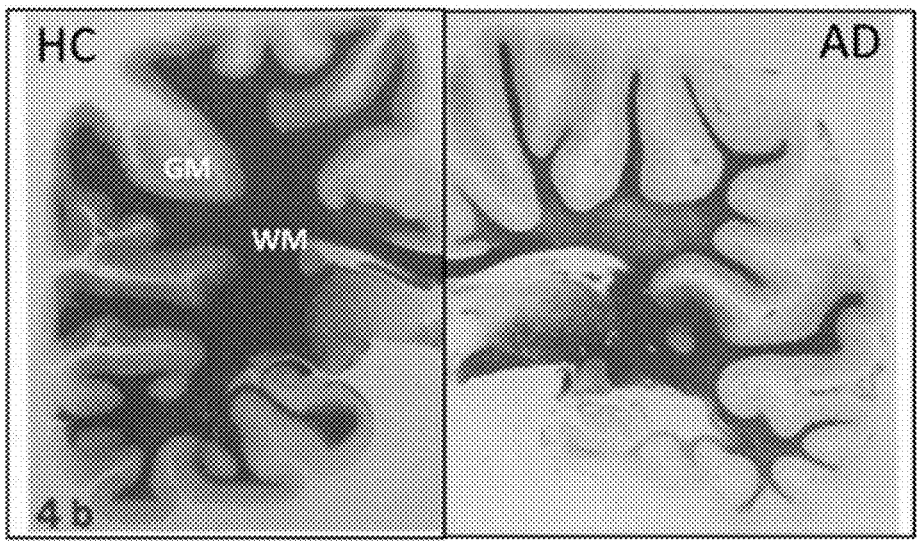
FIG. 26 is an image illustrating a comparison of a healthy control and an Alzheimer's disease brain.

But why study white matter? As shown in FIG. 26, which presents an image illustrating a comparison of a healthy control (HC) and an Alzheimer's disease (AD) brain, a large body of scientific literature has shown changes in white matter with Alzheimer's disease, such as: microglia activation, loss of oligodendrocytes, demyelination, axonal loss and vascular degeneration. It is now clear that the scientific community must look beyond the neuron and the cortex of the medial temporal lobe (where the hippocampus is located) and focus attention on white-matter integrity.

Figure 27A:
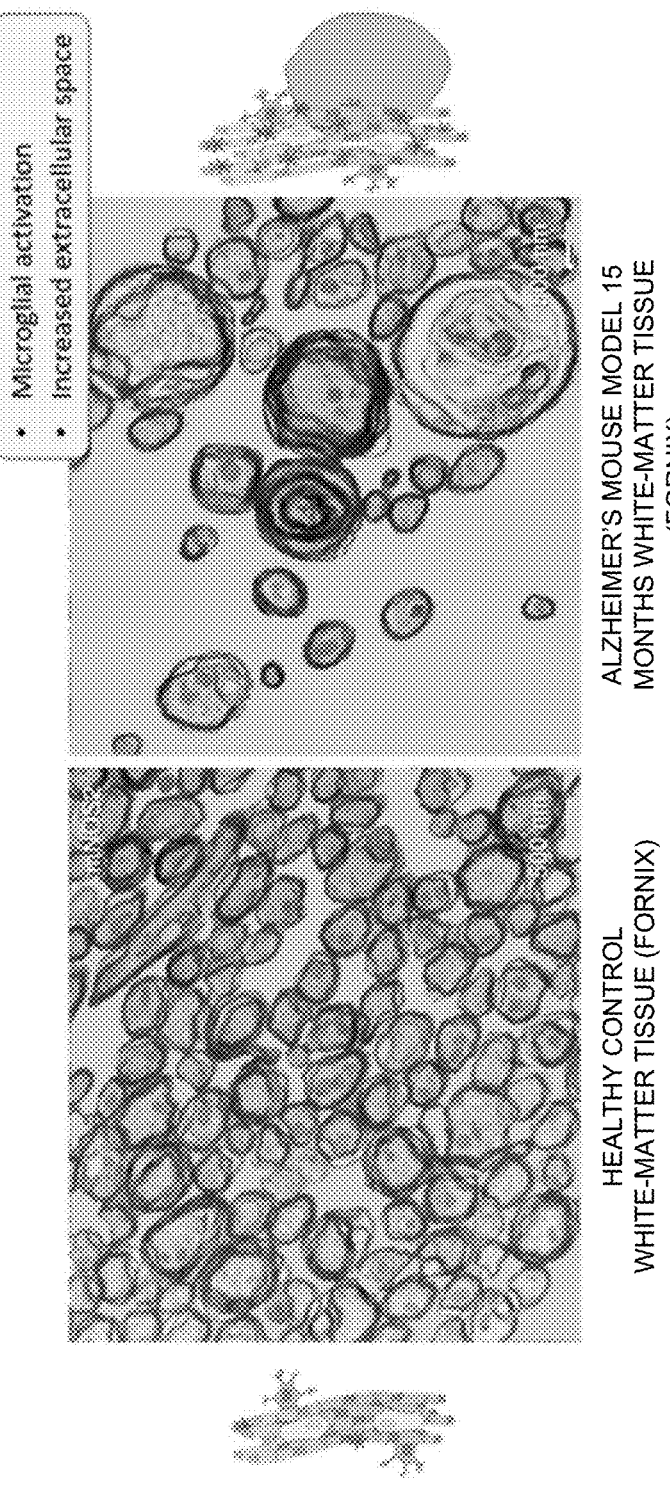
FIG. 27A is an image of white-matter axons in an animal study for healthy controls and Alzheimer's disease on histology illustrating free water and neuroinflammation.
Figure 27B:
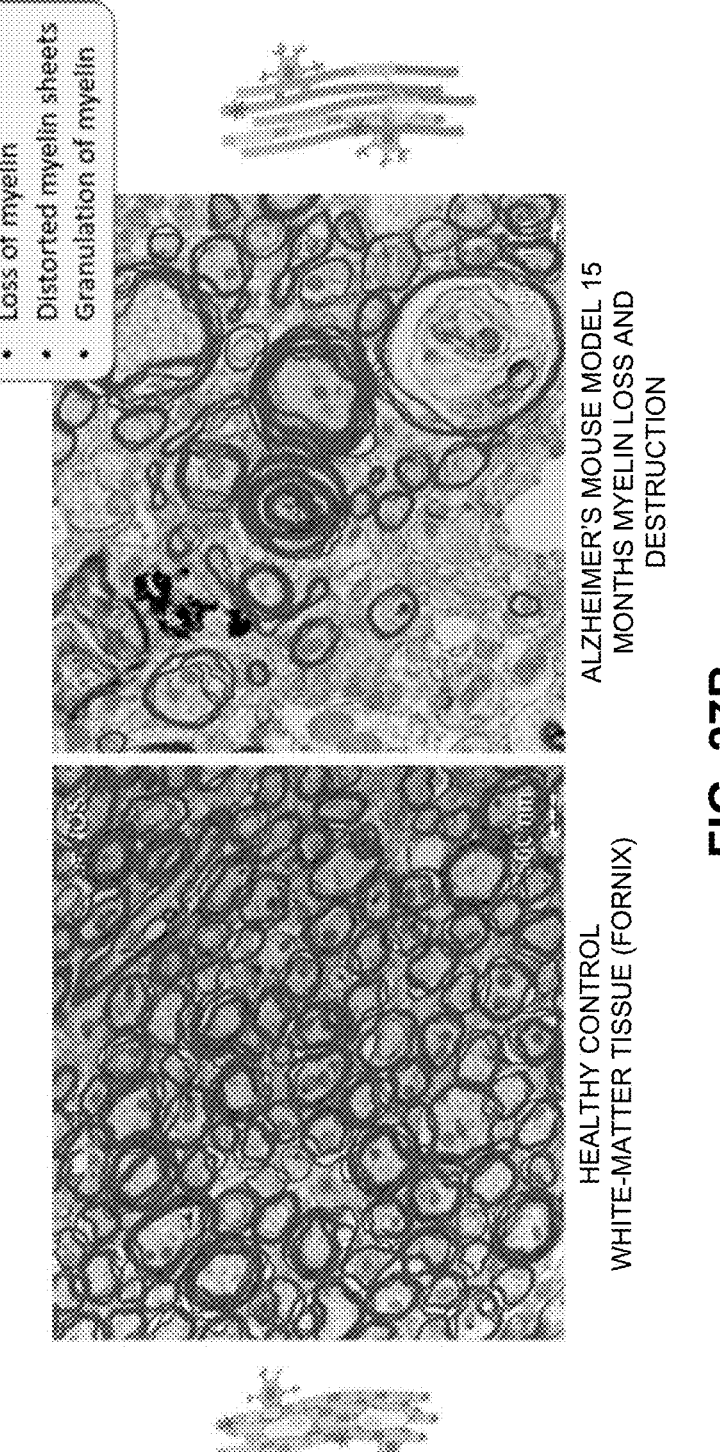
FIG. 27B is an image of white-matter axons in an animal study for healthy controls and Alzheimer's disease illustrating axon myelin degradation.
Figure 27C:
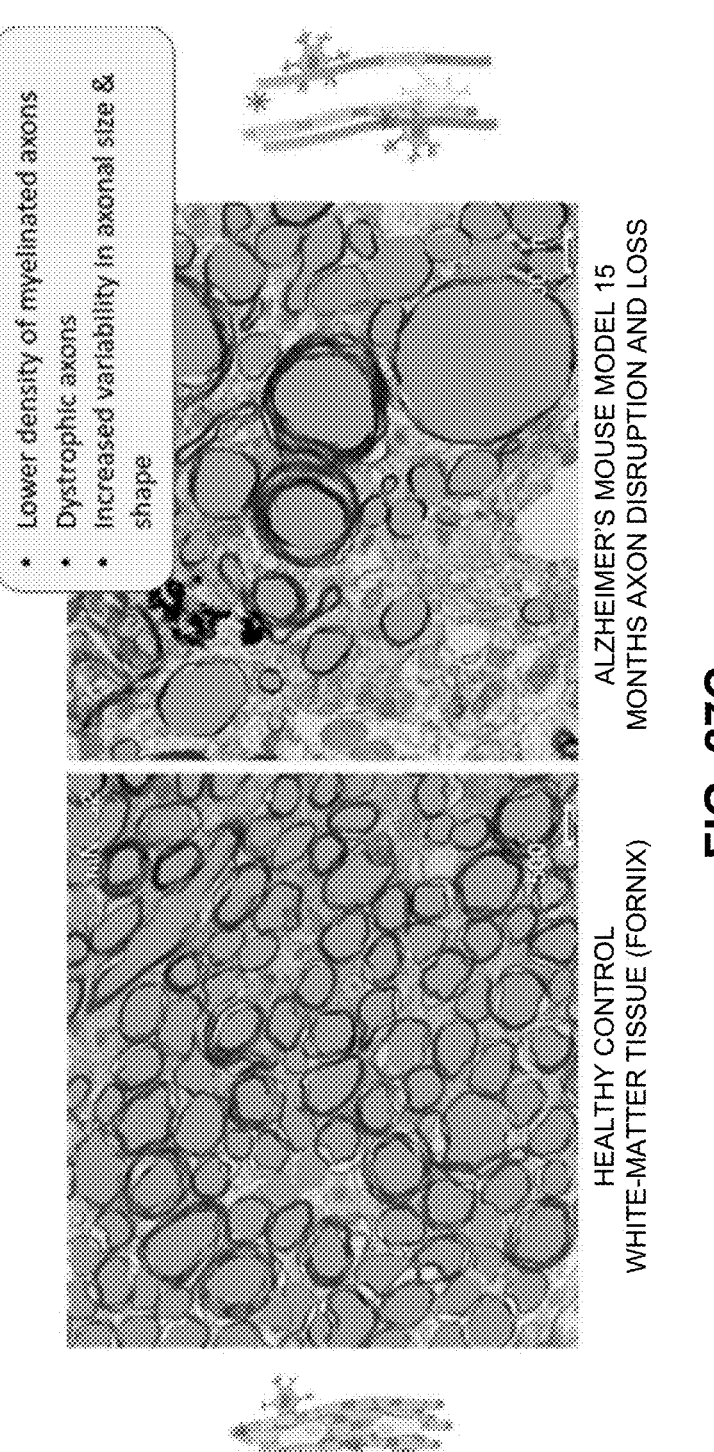
FIG. 27C is an image of white-matter axons in an animal study for healthy controls and Alzheimer's disease illustrating axon swelling.

White-matter abnormalities have been identified in several animal studies using high-resolution microscopy, histology and different staining techniques to highlight myelin, axons, and the extracellular space. Notably, studies of 15 months old Alzheimer's disease mice clearly highlight abnormalities in the white matter. For example, as shown in FIG. 27A, which presents an image of white-matter axons in an animal study for healthy controls and Alzheimer's disease on histology illustrating free water and neuroinflammation, there are increased extracellular space and microglia activation because of neuroinflammation. Moreover, as shown in FIG. 27B, which presents an image of white-matter axons in an animal study for healthy controls and Alzheimer's disease illustrating axon myelin degradation, there are loss of myelin, and distortion and granulation of the myelin sheets, which indicate myelin degradation or demyelination. Furthermore, as shown in FIG. 27C, which presents an image of white-matter axons in an animal study for healthy controls and Alzheimer's disease illustrating axon swelling, there are lower densities of myelinated axons, dystrophic axons, axon swelling and variability in size and shape of axons, which indicate axon disruption or axonal loss.

Figure 28:
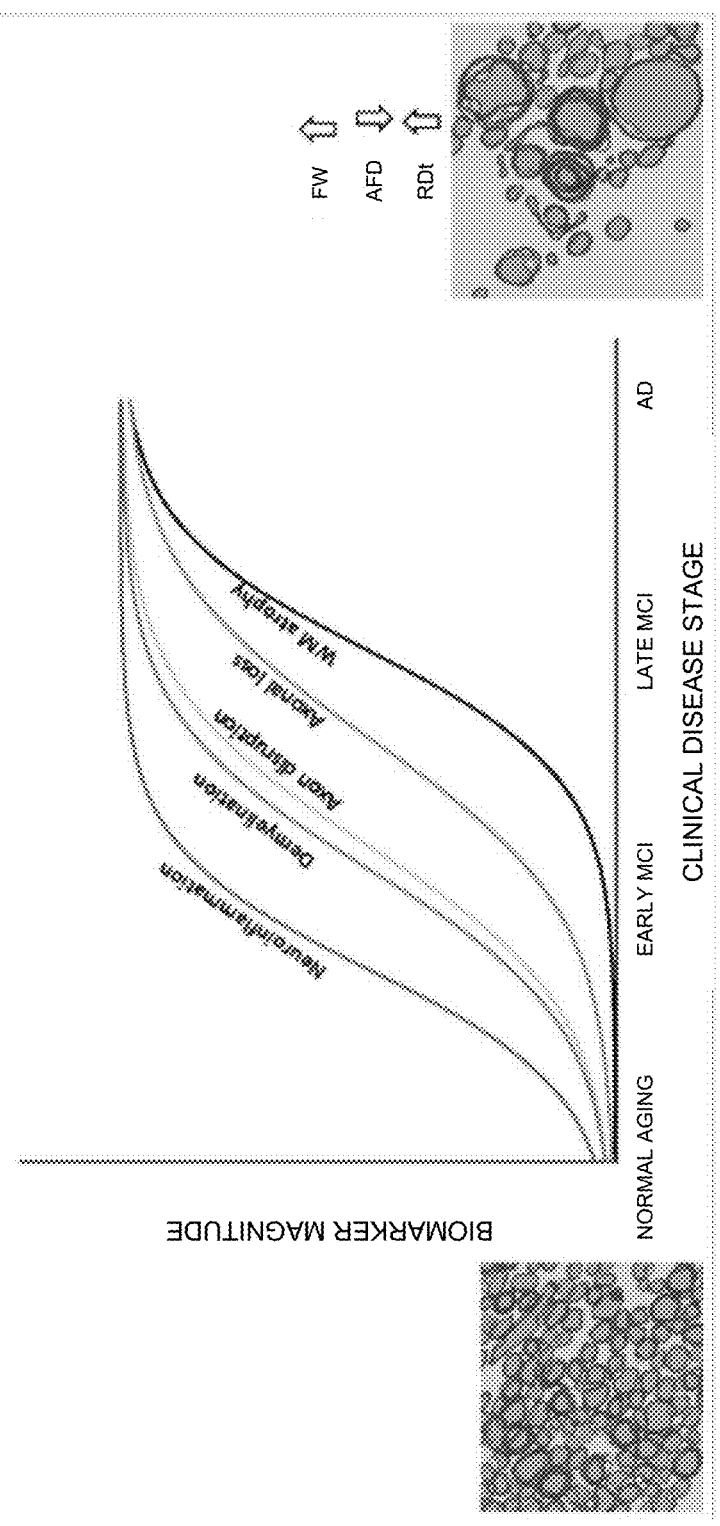
FIG. 28 is a drawing illustrating white-matter disease progression from a healthy control, to early/late mild cognitive impairment, and then to Alzheimer's disease.

Based on small animal and human studies, the progression of white-matter deterioration with Alzheimer's disease is now understood to be the result of a cascade of microstructural events. As shown in FIG. 28, which presents a drawing illustrating white-matter disease progression from a healthy control, to early/late mild cognitive impairment, and then to Alzheimer's disease, this process starts with neuroinflammation, followed by oligodendrocyte dysfunction, demyelination, axonal disruption and, ultimately, the death in the white matter, which causes white-matter atrophy and gray-matter atrophy. Note that the free water and the free water-corrected radial diffusivity (RDt) increase (conversely, the inverse free water-corrected RDt decreases), while the apparent fiber density decreases.

Figure 29:
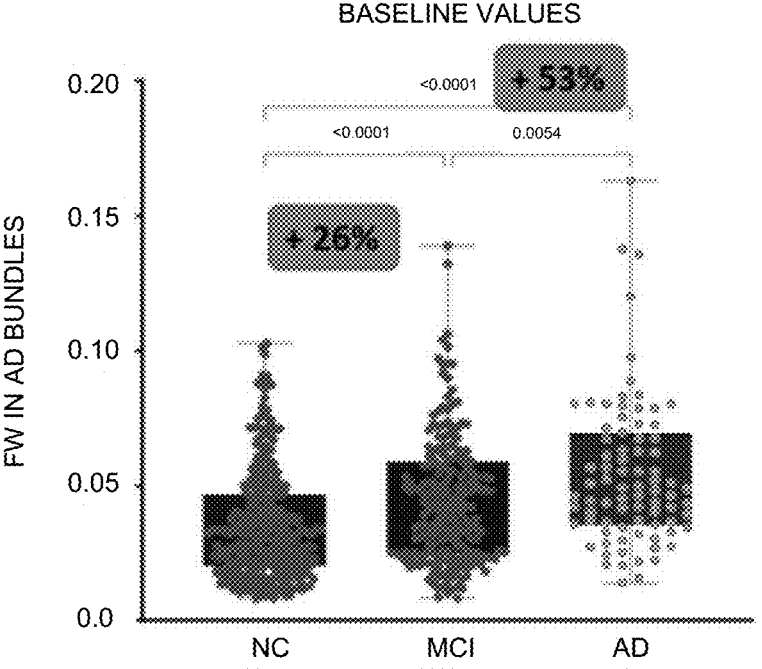
FIG. 29 is a drawing illustrating an example of free water in white-matter bundles in three groups of subjects, including healthy controls, mild cognitive impairment and Alzheimer's disease.
Figure 30:
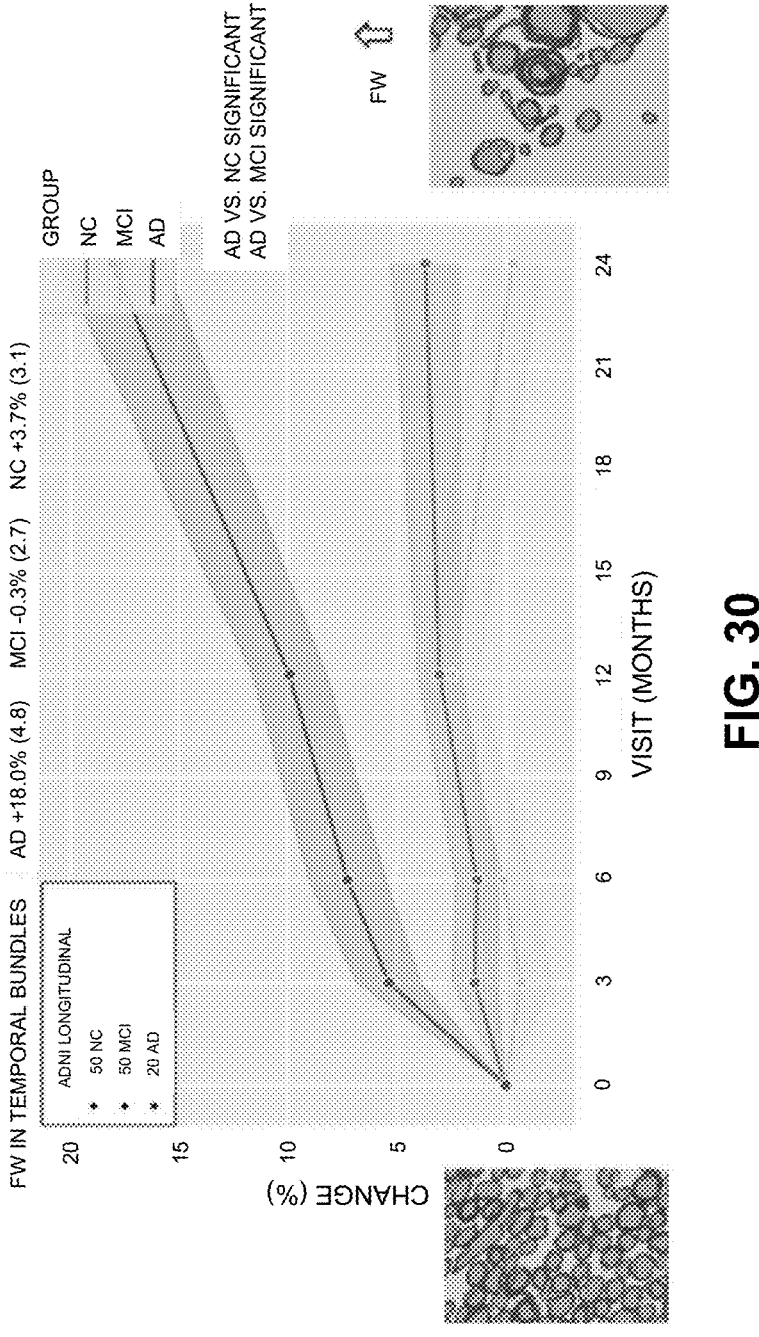
FIG. 30 is a drawing illustrating an example of free-water change as a function of time in white-matter bundles in the three groups of subjects.

As discussed previously, the set of white-matter disease biomarkers for Alzheimer's disease may include white-matter microstructure markers of neuroinflammation, demyelination and/or axonal disruption. Notably, the set of white-matter disease biomarkers computed using the analysis techniques may include free water, which is an indirect measure of neuroinflammation. The amount of free water may be very different between normal or healthy controls (NC), mild cognitive impairment (MCI), and Alzheimer's disease patients. For example, based on 500+ participants in the Alzheimer's disease neuroimaging initiative (ADNI) database, we have found that patients with mild cognitive impairment have 26% more free water than normal controls, while Alzheimer's disease patients have 53% more free water than normal controls. This is shown in FIG. 29, which presents a drawing illustrating an example of free water in white-matter bundles in three groups of subjects, including healthy controls, mild cognitive impairment and Alzheimer's disease. Moreover, free water also dramatically increases as a function of time for Alzheimer's disease patients (an 18% increase) compared to mild cognitive impairment and normal controls, which appear to be stable as a function of time. This is shown in FIG. 30, which presents a drawing illustrating an example of free-water change as a function of time in white-matter bundles in the three groups of subjects. Furthermore, free water appears to be a good biomarker to discriminate Alzheimer's disease patients. Once again, based on 500+ ADNI participants, receiver operator characteristic (ROC) analysis indicates that an individual with a free-water value greater than or equal to 0.04 has a 75% probability of being diagnosed with Alzheimer's disease.

Figure 31:
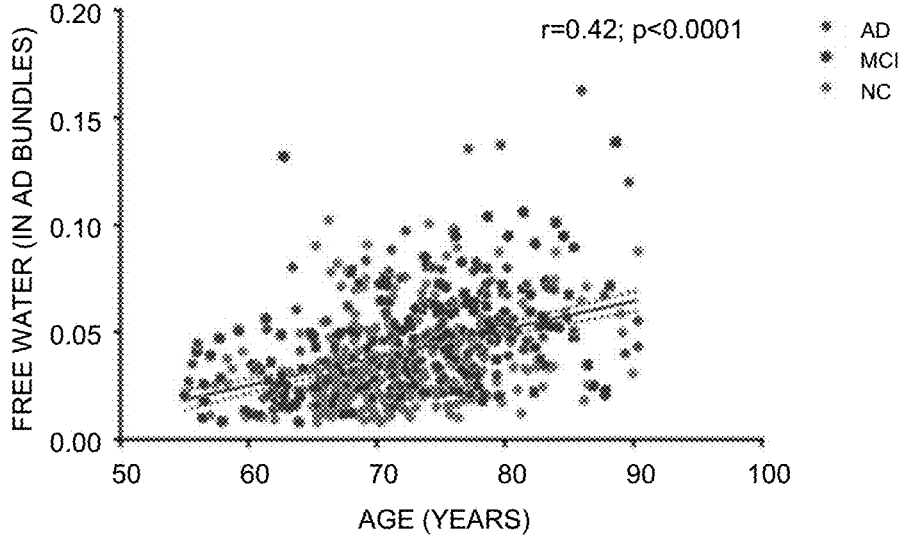
FIG. 31 is a drawing illustrating an example of correlation between free water and age.

Moreover, free water is correlated with age, which is an important risk factor for Alzheimer's disease. Indeed, statistics show that, at the age of 85 years old, a person has one in three probability of suffering from Alzheimer's disease. This is shown in FIG. 31, which presents a drawing illustrating an example of correlation between free water and age.

Figure 32A:
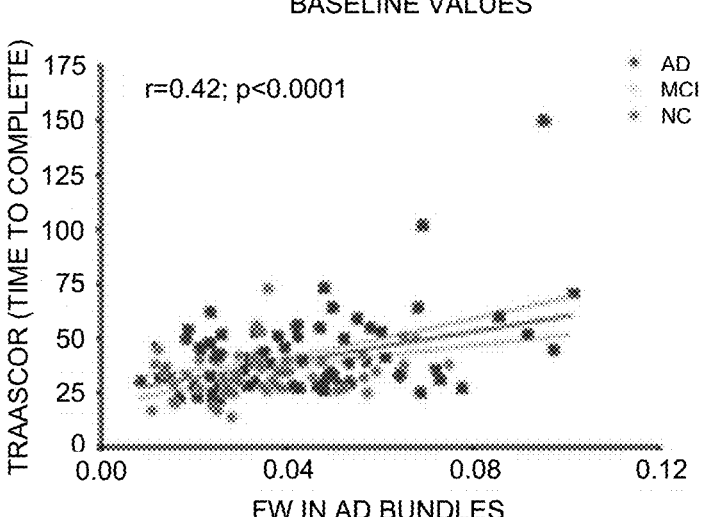
FIG. 32A-C are drawings illustrating examples of associations between free water and cognitive tests.
Figure 32B:
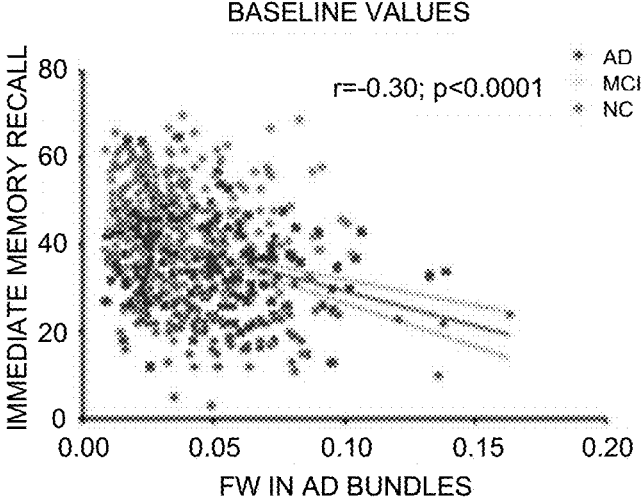
Figure 32C:
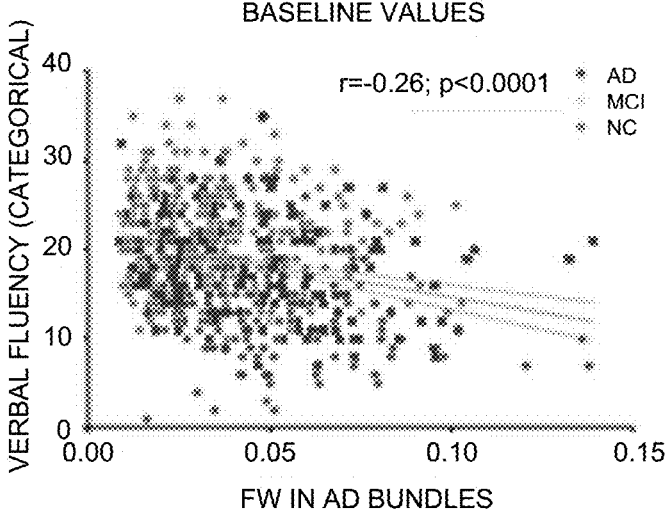

Furthermore, free water is very well anti-correlated with cognition. Notably, the Alzheimer's Disease Assessment Scale-Cognitive Subscale (ADAS-Cog13), an overall and global cognitive score is anti-correlated with free water. Stated differently, people performing poorly on this test have more free water (neuroinflammation) in their white matter. Similar associations are seen with processing speed, episodic memory, and fluency. These are shown in FIGS. 32A-C, which present drawings illustrating examples of associations between free water and cognitive tests. These results, therefore, suggest that free water may be a good biomarker, e.g., to select participants to enroll in clinical trials, depending on the drug effect and the group targeted. For example, in a clinical trial, an anti-inflammatory drug may be administered to patients that have a free water value above 0.1 (10%), which is indicative of patients that have too much neuroinflammation.

Additionally, free water may be a good biomarker for diagnosis, tracking disease progression and/or guiding treatment (such as a choice of medication and/or a dose). Notably, free water may serve as a biomarker to make sure a particular treatment does not increase neuroinflammation, but instead stabilize it or even decrease it over time. For example, an amyloid-clearing drug that effectively clears amyloid proteins from the brain, but that also increases neuroinflammation because of collateral damage, may not be a suitable treatment for affected patients.

The set of white-matter disease biomarkers for Alzheimer's disease may include demyelination. Demyelination may be indirectly measured by: the inverse free water-corrected radial diffusivity; other MRI myelin-specific markers (such as: $T_1/T_2$, a magnetization transfer ratio, etc.); and/or a myelin water fraction, which is the ratio of the area in the $T_2$ distribution (between 10 and 40 ms for humans) to the area of the entire $T_2$ distribution.

Figure 33:
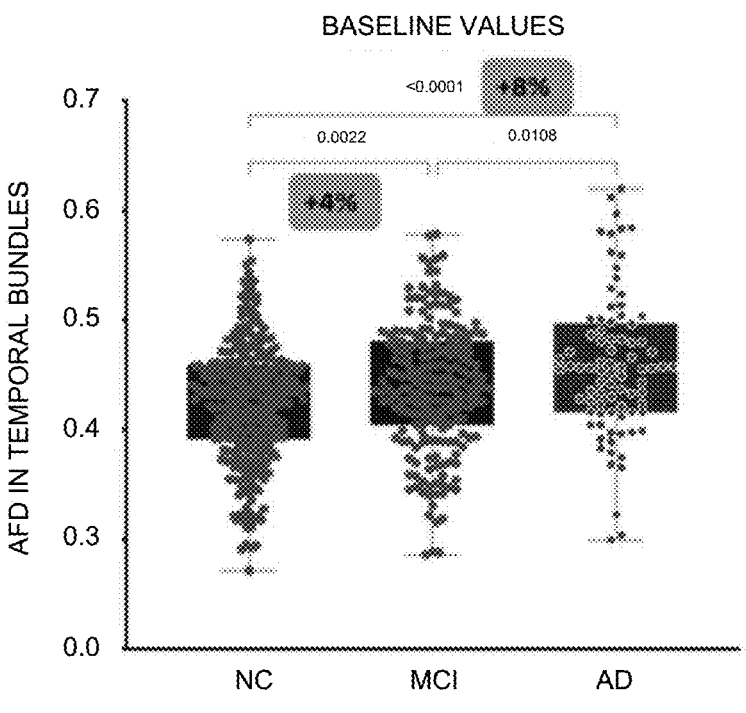
FIG. 33 is a drawing illustrating an example of apparent fiber density in the three groups of subjects.
Figure 34:
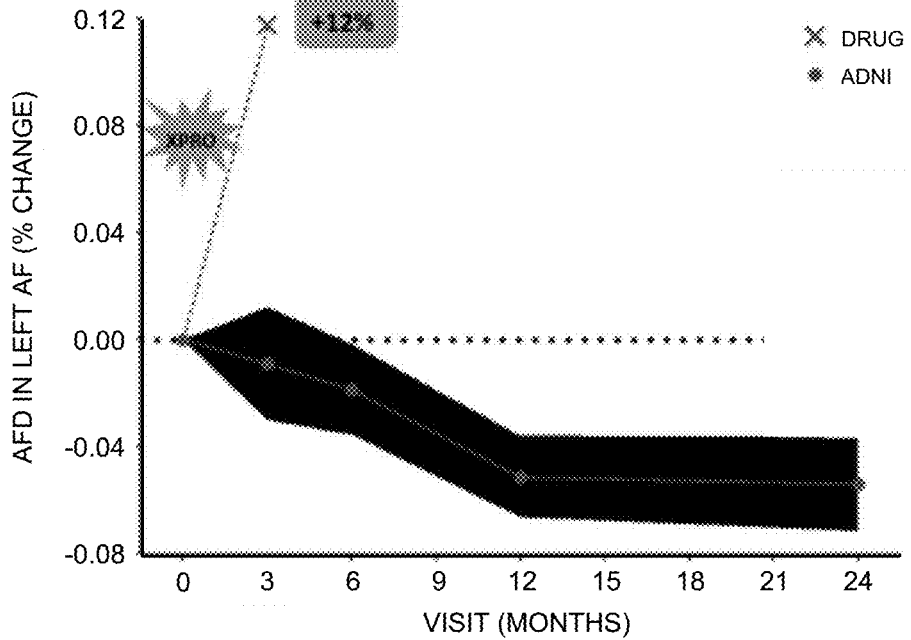
FIG. 34 is a drawing illustrating an example of a drug that increases the apparent fiber density of a patient.

Moreover, the set of white-matter disease biomarkers for Alzheimer's disease may include apparent fiber density, which is an indirect measure of axonal disruption and quality/tissue repair. Note that apparent fiber density may be slightly different for different disease stages. As shown in FIG. 33, which presents a drawing illustrating an example of apparent fiber density in the three groups of subjects, Alzheimer's disease patients may have apparent fiber density decrease 2-4% in time, which indicates axon disruption. In contrast, normal controls may have stable apparent fiber density over time. Furthermore, patients with mild cognitive impairment may have an inverted U-shape curve, which has been previously observed for other imaging biomarkers for these patients. This may be explained by axon swelling and the variable size and shape of axons that occur as white-matter disease progresses (see, e.g., FIG. 27B), which may be occurring in the mild-cognitive impairment group before axonal loss. Apparent fiber density may be very specific to white-matter changes and may be robust to crossing neurological fibers, as well as partial volume from other tissue. Additionally, apparent fiber density may be the biomarker of choice that a drug needs to stabilize (or even increase) in order to show tissue repair, better axon quality and potential remyelination. This is shown in FIG. 34, which presents a drawing illustrating an example of a drug that increases the apparent fiber density of a patient with Alzheimer's disease. Note that the drug: increased the apparent fiber density as a function of time (34/35 bundles, with an average increase of 8%). Moreover, for ADNI bundles, the arcuate fasciculus (AF), the inferior fronto-occipital fasciculus (IFOF) and the inferior longitudinal fasciculus (ILF) increased by 11%.

Figure 35:
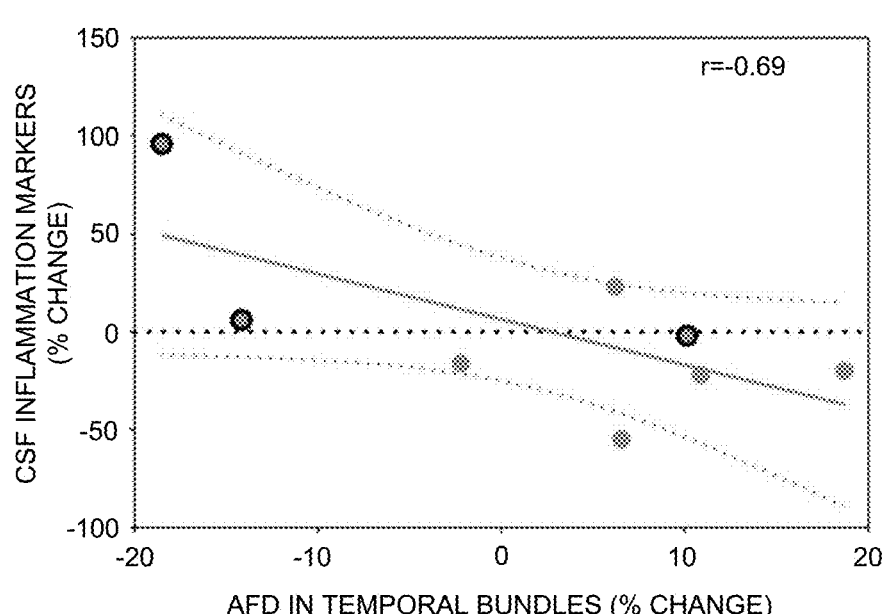
FIG. 35 is a drawing illustrating an example of associations between apparent fiber density and cerebrospinal-fluid inflammatory markers.

As shown in FIG. 35, which presents a drawing illustrating an example of associations between apparent fiber density and cerebrospinal-fluid inflammatory markers, apparent fiber density is strongly correlated with cerebrospinal-fluid inflammatory markers. This shows that, the more inflammation is reduced, the healthier the axons (as indicated by apparent fiber density). Note that apparent fiber density has also been shown to correlate with traumatic brain injury (e.g., in professional football players).

In some embodiments, the combination of the hippocampus volume with the set of white-matter disease biomarkers (such as the neuroinflammation, demyelination and/or axonal disruption metrics) helps improve the correlation score with Alzheimer's disease progression. Moreover, one or more of the set of white-matter disease biomarkers may be computed on a per-voxel basis and/or a per-neurological-fiber (or fixel) basis. In these ways, diseases can be characterized based at least in part on their overall effect on the white matter, on sub-regions or neurological anatomical regions of the brain (such as the corpus callosum, inferior fronto-occipital fasciculus and arcuate fasciculus for Alzheimer's disease, motor tracts for Parkinson's disease, and the medial temporal lobe for mild cognitive impairment), on a per-voxel and/or on a per-fixel basis.

The set of white-matter disease biomarkers may allow the computer system to determine the stage of a disease. As such, for a given Alzheimer's disease patient at a particular time, a physician may prescribe an anti-inflammatory drug, a remyelinating drugs, or a stabilization drug depending on the neuroinflammation, demyelination and/or axonal disruption scores of metrics for this patient. Similar feedback information may be provided by the computer system for one or more other neurological diseases, such as: Parkinson's disease, multiple sclerosis, Amyotrophic lateral sclerosis, etc.

Figure 36:
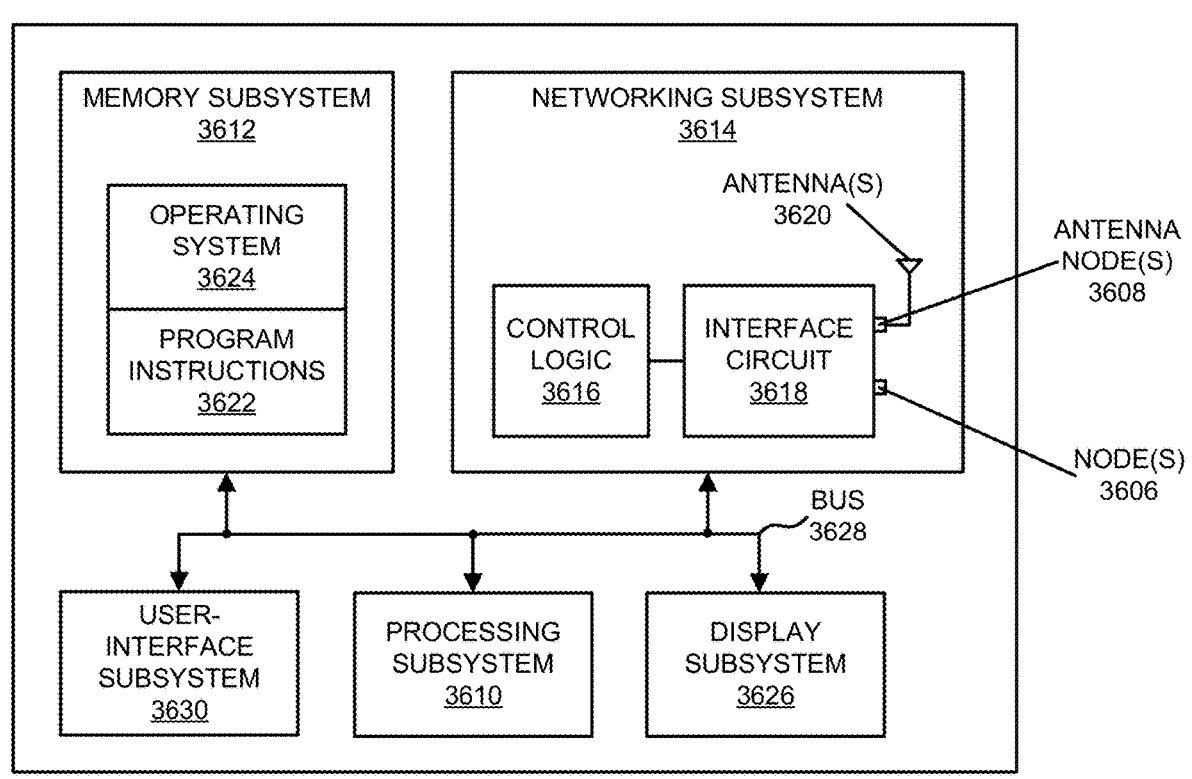
FIG. 36 is a block diagram illustrating an example of a computer in accordance with an embodiment of the present disclosure.

We now describe embodiments of a computer, which may perform at least some of the operations in the analysis techniques. FIG. 36 presents a block diagram illustrating an example of a computer 3600, e.g., in a computer system (such as computer system 100 in FIG. 1), in accordance with some embodiments. For example, computer 3600 may include: one of computers 110. This computer may include processing subsystem 3610, memory subsystem 3612, and networking subsystem 3614. Processing subsystem 3610 includes one or more devices configured to perform computational operations. For example, processing subsystem 3610 can include one or more microprocessors, ASICs, microcontrollers, programmable-logic devices, GPUs and/ or one or more DSPs. Note that a given component in processing subsystem 3610 are sometimes referred to as a 'computation device'.

Memory subsystem 3612 includes one or more devices for storing data and/or instructions for processing subsystem 3610 and networking subsystem 3614. For example, memory subsystem 3612 can include dynamic random access memory (DRAM), static random access memory (SRAM), and/or other types of memory. In some embodiments, instructions for processing subsystem 3610 in memory subsystem 3612 include: program instructions or sets of instructions (such as program instructions 3622 or operating system 3624), which may be executed by processing subsystem 3610. Note that the one or more computer programs or program instructions may constitute a computer-program mechanism. Moreover, instructions in the various program instructions in memory subsystem 3612 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 3610.

In addition, memory subsystem 3612 can include mechanisms for controlling access to the memory. In some embodiments, memory subsystem 3612 includes a memory hierarchy that comprises one or more caches coupled to a memory in computer 3600. In some of these embodiments, one or more of the caches is located in processing subsystem 3610.

In some embodiments, memory subsystem 3612 is coupled to one or more high-capacity mass-storage devices (not shown). For example, memory subsystem 3612 can be coupled to a magnetic or optical drive, a solid-state drive, or another type of mass-storage device. In these embodiments, memory subsystem 3612 can be used by computer 3600 as fast-access storage for often-used data, while the mass-storage device is used to store less frequently used data.

Networking subsystem 3614 includes one or more devices configured to couple to and communicate on a wired and/or wireless network (i.e., to perform network operations), including: control logic 3616, an interface circuit 3618 and one or more antennas 3620 (or antenna elements). (While FIG. 36 includes one or more antennas 3620, in some embodiments computer 3600 includes one or more nodes, such as antenna nodes 3608, e.g., a metal pad or a connector, which can be coupled to the one or more antennas 3620, or nodes 3606, which can be coupled to a wired or optical connection or link. Thus, computer 3600 may or may not include the one or more antennas 3620. Note that the one or more nodes 3606 and/or antenna nodes 3608 may constitute input(s) to and/or output(s) from computer 3600.) For example, networking subsystem 3614 can include a Bluetooth™ networking system, a cellular networking system (e.g., a 3G/4G/5G network such as UMTS, LTE, etc.), a universal serial bus (USB) networking system, a networking system based on the standards described in IEEE 802.11 (e.g., a Wi-Fi® networking system), an Ethernet networking system, and/or another networking system.

Networking subsystem 3614 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between the electronic devices does not yet exist. Therefore, computer 3600 may use the mechanisms in networking subsystem 3614 for performing simple wireless communication between electronic devices, e.g., transmitting advertising or beacon frames and/or scanning for advertising frames transmitted by other electronic devices.

Within computer 3600, processing subsystem 3610, memory subsystem 3612, and networking subsystem 3614 are coupled together using bus 3628. Bus 3628 may include an electrical, optical, and/or electro-optical connection that the subsystems can use to communicate commands and data among one another. Although only one bus 3628 is shown for clarity, different embodiments can include a different number or configuration of electrical, optical, and/or electro-optical connections among the sub systems.

In some embodiments, computer 3600 includes a display subsystem 3626 for displaying information on a display, which may include a display driver and the display, such as a liquid-crystal display, a multi-touch touchscreen, etc. Moreover, computer 3600 may include a user-interface subsystem 3630, such as: a mouse, a keyboard, a trackpad, a stylus, a voice-recognition interface, and/or another human-machine interface.

Computer 3600 can be (or can be included in) any electronic device with at least one network interface. For example, computer 3600 can be (or can be included in): a desktop computer, a laptop computer, a subnotebook/netbook, a server, a supercomputer, a tablet computer, a smartphone, a cellular telephone, a consumer-electronic device, a portable computing device, communication equipment, and/ or another electronic device.

Although specific components are used to describe computer 3600, in alternative embodiments, different components and/or subsystems may be present in computer 3600. For example, computer 3600 may include one or more additional processing subsystems, memory subsystems, networking subsystems, and/or di splay subsystems. Additionally, one or more of the subsystems may not be present in computer 3600. Moreover, in some embodiments, computer 3600 may include one or more additional subsystems that are not shown in FIG. 36. Also, although separate subsystems are shown in FIG. 36, in some embodiments some or all of a given subsystem or component can be integrated into one or more of the other subsystems or component(s) in computer 3600. For example, in some embodiments program instructions 3622 are included in operating system 3624 and/or control logic 3616 is included in interface circuit 3618.

Moreover, the circuits and components in computer 3600 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 3614 and/or computer 3600. The integrated circuit may include hardware and/or software mechanisms that are used for transmitting signals from computer 3600 and receiving signals at computer 3600 from other electronic devices. Aside from the mechanisms herein described, radios are generally known in the art and hence are not described in detail. In general, networking subsystem 3614 and/or the integrated circuit may include one or more radios.

In some embodiments, an output of a process for designing the integrated circuit, or a portion of the integrated circuit, which includes one or more of the circuits described herein may be a computer-readable medium such as, for example, a magnetic tape or an optical or magnetic disk or solid state disk. The computer-readable medium may be encoded with data structures or other information describing circuitry that may be physically instantiated as the integrated circuit or the portion of the integrated circuit. Although various formats may be used for such encoding, these data structures are commonly written in: Caltech Intermediate Format (CIF), Calma GDS II Stream Format (GDSII), Electronic Design Interchange Format (EDIF), OpenAccess (OA), or Open Artwork System Interchange Standard (OASIS). Those of skill in the art of integrated circuit design can develop such data structures from schematics of the type detailed above and the corresponding descriptions and encode the data structures on the computer-readable medium. Those of skill in the art of integrated circuit fabrication can use such encoded data to fabricate integrated circuits that include one or more of the circuits described herein.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the analysis techniques may be implemented using program instructions 3622, operating system 3624 (such as a driver for interface circuit 3618) or in firmware in interface circuit 3618. Thus, the analysis techniques may be implemented at runtime of program instructions 3622. Alternatively or additionally, at least some of the operations in the analysis techniques may be implemented in a physical layer, such as hardware in interface circuit 3618.

In the preceding description, we refer to 'some embodiments'. Note that 'some embodiments' describes a subset of all of the possible embodiments, but does not always specify the same subset of embodiments. Moreover, note that the numerical values provided are intended as illustrations of the analysis techniques. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer system, comprising:
a computation device;
memory configured to store program instructions, wherein, when executed by the computation device, the program instructions cause the computer system to perform one or more operations comprising:
receiving medical-imaging data associated with at least an individual;
computing, based at least in part on the medical-imaging data, a set of white-matter disease biomarkers for different neurological anatomical regions, wherein, for a given neurological anatomical region, the set of white-matter disease biomarkers comprises: an apparent fiber density that corresponds to a total intra-axonal volume, an amount of free water that consists of intracellular water, and a demyelination metric; and
providing feedback information associated with at least the individual based at least in part on interrelationships among the computed set of white-matter disease biomarkers in different neurological anatomical regions, wherein, for Alzheimer's disease, Parkinson's disease, multiple sclerosis or traumatic brain injury, the interrelationships comprise: an increase in the amount of free water, a decrease in the apparent fiber density and an increase in the demyelination.

2. The computer system of claim 1, wherein the amount of free water corresponds to neuroinflammation.

3. The computer system of claim 1, wherein the apparent fiber density corresponds to axonal disruption or axonal quality.

4. The computer system of claim 1, wherein the demyelination metric comprises: an inverse free-water-corrected radial diffusivity, a ratio of spin-lattice relaxation time ($T_1$) to spin-spin relaxation time ($T_2$), a magnetization transfer ratio, or a myelin water fraction (MWF); and
wherein the MWF comprises a ratio of a signal amplitude associated with a myelin water compartment to a sum of the signal amplitude associated with the myelin water compartment and a signal amplitude associated with an extra-intra cellular water compartment.

5. The computer system of claim 1, wherein the set of white-matter disease biomarkers is computed on a per-voxel basis, a per-neurological-fiber basis, or both.

6. The computer system of claim 1, wherein the medical-imaging data comprises diffusion magnetic resonance imaging (dMRI) data, magnetization transfer MRI, or quantitative MRI.

7. The computer system of claim 1, wherein the feedback information comprises: diagnostic information, information associated with disease progression, information regarding efficacy of a treatment, or a treatment recommendation.

8. The computer system of claim 7, wherein the diagnostic information is associated with a neurological disease comprising: multiple sclerosis, Alzheimer's disease, Parkinson's disease, amyotrophic lateral sclerosis, traumatic brain injury, or another neurodegenerative disease.

9. The computer system of claim 1, wherein the feedback information is based at least in part on a volume of a neurological anatomical region in at least the individual.

10. The computer system of claim 9, wherein the neurological anatomical region comprises the hippocampus.

11. The computer system of claim 1, wherein the medical-imaging data is associated with a population of cases and controls, either of which comprises at least the individual, and the feedback information is associated with the population.

12. The computer system of claim 1, wherein the feedback information is determined using a pretrained predictive model; and wherein the pretrained predictive model comprises: a machine-learning model or a neural network.

13. A non-transitory computer-readable storage medium for use in conjunction with a computer system, the computer-readable storage medium configured to store program instructions that, when executed by the computer system, causes the computer system to perform one or more operations comprising:

receiving medical-imaging data associated with at least an individual;

computing, based at least in part on the medical-imaging data, a set of white-matter disease biomarkers for different neurological anatomical regions, wherein, for a given neurological anatomical region, the set of white-matter disease biomarkers comprises: an apparent fiber density that corresponds to a total intra-axonal volume, an amount of free water that consists of intracellular water, and a demyelination metric; and providing feedback information associated with at least the individual based at least in part on interrelationships among the computed set of white-matter disease biomarkers in different neurological anatomical regions, wherein, for Alzheimer's disease, Parkinson's disease, multiple sclerosis or traumatic brain injury, the interrelationships comprise: an increase in the amount of free water, a decrease in the apparent fiber density and an increase in the demyelination.

14. The non-transitory computer-readable storage medium of claim 13, wherein the set of white-matter disease biomarkers is computed on a per-voxel basis, a per-neurological-fiber basis, or both.

15. The non-transitory computer-readable storage medium of claim 13, wherein the feedback information comprises: diagnostic information, information associated with disease progression, information regarding efficacy of a treatment, or a treatment recommendation.

16. A method for providing feedback information, comprising:

by a computer system:

receiving medical-imaging data associated with at least an individual;

computing, based at least in part on the medical-imaging data, a set of white-matter disease biomarkers for different neurological anatomical regions, wherein, for a given neurological anatomical region, the set of white-matter disease biomarkers comprises: an apparent fiber density that corresponds to a total intra-axonal volume, an amount of free water that consists of intracellular water, and a demyelination metric; and providing the feedback information associated with at least the individual based at least in part on interrelationships among the computed set of white-matter disease biomarkers in different neurological anatomical regions, wherein, for Alzheimer's disease, Parkinson's disease, multiple sclerosis or traumatic brain injury, the interrelationships comprise: an increase in the amount of free water, a decrease in the apparent fiber density and an increase in the demyelination.

17. The method of claim 16, wherein the set of white-matter disease biomarkers is computed on a per-voxel basis, a per-neurological-fiber basis, or both.

18. The method of claim 16, wherein the feedback information comprises: diagnostic information, information associated with disease progression, information regarding efficacy of a treatment, or a treatment recommendation.

19. The method of claim 16, wherein the amount of free water corresponds to neuroinflammation.

20. The method of claim 16, wherein the apparent fiber density corresponds to axonal disruption or axonal quality.

* * * * *